(12) United States Patent
Nishida et al.

(10) Patent No.: US 12,272,459 B2
(45) Date of Patent: Apr. 8, 2025

(54) MEDICAL DIAGNOSTIC APPARATUS AND METHOD FOR EVALUATION OF PATHOLOGICAL CONDITIONS USING 3D DATA AND IMAGES OF LAMINA CRIBROSA

(71) Applicants: Topcon Corporation, Tokyo (JP); Osaka University, Osaka (JP)

(72) Inventors: Kohji Nishida, Osaka (JP); Atsuya Miki, Osaka (JP); Kazuichi Maruyama, Osaka (JP); Ryo Kawasaki, Osaka (JP); Song Mei, Tokyo (JP); Zaixing Mao, Tokyo (JP); Zhenguo Wang, Tokyo (JP); Kinpui Chan, Tokyo (JP); Xin Sui, Tokyo (JP)

(73) Assignees: Topcon Corporation, Tokyo (JP); Osaka University, Osaka (JP)

(*) Notice: Subject to any disclaimer, the term of this patent is extended or adjusted under 35 U.S.C. 154(b) by 632 days.

(21) Appl. No.: 17/493,856

(22) Filed: Oct. 5, 2021

(65) Prior Publication Data
US 2023/0105247 A1   Apr. 6, 2023

(51) Int. Cl.
*G06T 7/12* (2017.01)
*G06T 7/10* (2017.01)
(Continued)

(52) U.S. Cl.
CPC .............. *G16H 50/20* (2018.01); *G06T 7/10* (2017.01); *G06T 15/08* (2013.01); *G16H 50/30* (2018.01);
(Continued)

(58) Field of Classification Search
USPC ........ 128/920–925; 351/200–243; 356/2–22, 356/484–521, 625–640; 382/100–180,
(Continued)

(56) References Cited

U.S. PATENT DOCUMENTS

| 9,265,418 B2* | 2/2016 | Iwase .................... A61B 3/14 |
| 10,973,406 B2* | 4/2021 | Imamura ............... A61B 3/102 |

(Continued)

FOREIGN PATENT DOCUMENTS

| EP | 2742856 A1 | 6/2014 |
| EP | 3591614 A1 | 1/2020 |
| EP | 3633604 A1 | 4/2020 |

OTHER PUBLICATIONS

Iwase Yoshihiko; Medical Image Processing Device, Learned Model, Medical Image Processing Method and Program; 2020 (Year: 2020).*

(Continued)

*Primary Examiner* — Marcellus J Augustin
(74) *Attorney, Agent, or Firm* — XSENSUS LLP

(57) ABSTRACT

A medical diagnostic apparatus includes a receiver circuit that receives three-dimensional data of a subject's eye, and a processor configured to separate portions of the three-dimensional data into separate segments, perform processing differently on each of the separate segments, and combine the separately processed segments to produce a segmented three-dimensional data set. The processor is further configured to generate at least one diagnostic metric from the segmented three-dimensional data set, and the processor is further configured to evaluate a pathological condition based on the at least one diagnostic metric. Related methods and computer readable media are also disclosed.

19 Claims, 11 Drawing Sheets

(51) Int. Cl.
    *G06T 15/08*     (2011.01)
    *G16H 50/20*     (2018.01)
    *G16H 50/30*     (2018.01)

(52) U.S. Cl.
    CPC .............. *G06T 2207/10101* (2013.01); *G06T 2207/30041* (2013.01)

(58) Field of Classification Search
    USPC ................ 382/218–225; 706/1–62, 900–903
    See application file for complete search history.

(56) References Cited

U.S. PATENT DOCUMENTS

| | | | | |
|---|---|---|---|---|
| 2002/0186818 | A1* | 12/2002 | Arnaud | G06Q 30/02 378/165 |
| 2013/0194546 | A1 | 8/2013 | Iwase | |
| 2013/0258285 | A1* | 10/2013 | Iwase | A61B 3/102 351/246 |
| 2014/0152957 | A1* | 6/2014 | Reisman | G06T 7/0012 351/246 |
| 2014/0362344 | A1* | 12/2014 | Imamura | G06T 7/0012 351/246 |
| 2017/0273557 | A1 | 9/2017 | Nakazawa et al. | |
| 2019/0274542 | A1 | 9/2019 | Imamura et al. | |

OTHER PUBLICATIONS

Brandt Alexander; Method for Automatic Shape Quantification of an Optic Nerve Head; 2020 (Year: 2020).*
Downs et al., "Lamina Cribrosa in Glaucoma", HHS Public Access, Curr Opin Ophthalmol, vol. 28, No. 2, Mar. 2017, pp. 113-119.
Mao et al. "Deep Learning Based Noise Reduction Method for Automatic 3D Segmentation of the Anterior of Lamina Cribrosa in Optical Coherence Tomography Volumetric Scans", Biomedical Optics Express, vol. 10, No. 11, Nov. 1, 2019, pp. 5832-5851.
Chen et al., "XGBoost: A Scalable Tree Boosting System", arXiv:1603. 02754v3, Jun. 10, 2016, 13 pages.
Extended European search report issued on Feb. 20, 2023, in corresponding European patent Application No. 22186449.9, 8 pages.

* cited by examiner

| Metric | Category | Shorthand name | Explanation |
|---|---|---|---|
| Depth of the lowest point | Depth | Low | Depth of lowest point, relative to BMO reference plane |
| Depth of the highest point | Depth | High | Depth of highest point, relative to BMO reference plane |
| X coordinate of the lowest point | Location | Lx | X coordinate of lowest point (in pixel) |
| Y coordinate of the lowest point | Location | Ly | Y coordinate of lowest point (in pixel) |
| X coordinate of the highest point | Location | Hx | X coordinate of highest point (in pixel) |
| Y coordinate of the highest point | Location | Hy | Y coordinate of highest point (in pixel) |
| Volume | Volume | Vol | Volume between BMO reference plane and anterior LC surface |
| BMO area | Area | Bmo | Area of BMO contour |
| Average depth | Depth | Avg_d | Average depth of anterior LC surface to BMO reference plane. avg_d= vol / bmo |
| Distance mean | Surface roughness | D_mean | Mean of differences between anterior LC surface with the polynomial best-fitting smooth surface |
| Distance std | Surface roughness | D_std | standard deviation of differences between anterior LC surface with the polynomial best-fitting smooth surface |
| R mean | Line curvature | R_mean | Mean of line curvatures of anterior LC surface |
| R std | Line curvature | R_std | Standard deviation of anterior LC surface |
| 3D surface area | Area | Area3 | 3d surface area of anterior LC surface |
| 2D surface area | Area | Area2 | 2d area of anterior LC surface projection on the reference plane |
| Ratio | Surface roughness | Ratio | a measure of roughness: ratio = area3 / area2 |

FIG. 4

MEDICAL DIAGNOSTIC APPARATUS AND METHOD FOR EVALUATION OF PATHOLOGICAL CONDITIONS USING 3D DATA AND IMAGES OF LAMINA CRIBROSA

FIELD OF THE INVENTION

The present disclosure relates generally to analysis of data and images for monitoring, evaluation, and diagnosis of medical conditions, and in particular to the analysis of three-dimensional (3D) optical coherence tomography (OCT) data and images of the lamina cribrosa for monitoring, evaluation, and diagnosis of medical conditions.

BACKGROUND OF INVENTION

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

OCT is a technique for in-vivo imaging and analysis of various biological tissues (as, for example, two-dimensional slices and/or three-dimensional volumes). Images created from three-dimensional (3D)/volumetric OCT data show different appearances/brightness for different components of the imaged tissue. Based on this difference, those components can be segmented out from the images for further analysis and/or visualization. However, due to inherent properties of OCT imaging, artifacts in segmentation may emerge if the thresholding is directly applied to the images.

SUMMARY OF INVENTION

An embodiment of the invention includes a medical diagnostic apparatus having a receiver circuit that receives three-dimensional data of a subject's eye; a processor configured to separate portions of the three-dimensional data into separate segments, perform processing differently on each of the separate segments, and combine the separately processed segments to produce a segmented three-dimensional data set; the processor is further configured to generate at least one diagnostic metric from the segmented three-dimensional data set; and the processor is further configured to evaluate a medical condition based on the at least one diagnostic metric.

In the medical diagnostic apparatus the processor may be configured to generate a visualization to render a three dimensional view of the diagnostic metric In the medical diagnostic apparatus the at least one diagnostic metric may include at least one physical characteristic of a Bruch's Membrane Opening in the subject's eye.

In the medical medical diagnostic apparatus the at least one diagnostic metric may include at least one physical characteristic of a lamina cribrosa in the subject's eye.

In the medical diagnostic apparatus the at least one diagnostic metric may include at least one physical characteristic calculated based on a Bruch's Membrane Opening and a lamina cribrosa in the subject's eye.

In the medical diagnostic apparatus the processor may identify a reference plane maximally correlated with a largest surface of a Bruch's Membrane Opening in the subject's eye; the processor may identify a smooth polynomial maximally correlated with an anterior surface of a lamina cribrosa in the subject's eye; and the at least one diagnostic metric may include a measurement based on the reference plane and the smooth polynomial.

In the medical diagnostic apparatus the processor may identify a reference plane maximally correlated with a largest surface of a Bruch's Membrane Opening in the subject's eye; and the at least one diagnostic metric may include at least one of a depth of a lowest point on an anterior surface of a lamina cribrosa in the subject's eye that is furthest from the reference plane, a depth of a highest point on the anterior surface of the lamina cribrosa that is closest to the reference plane, an X coordinate of the lowest point in an X/Y coordinate system of an optical coherence tomography scanner that generates the three-dimensional data, a Y coordinate of the lowest point in the X/Y coordinate system, an X coordinate of the highest point in the X/Y coordinate system, a Y coordinate of the highest point in the X/Y coordinate system, a volume of a space between the reference plane and the anterior surface of the lamina cribrosa, an area of a contour of the Bruch's Membrane Opening projected to the reference plane, an average depth of points on the anterior surface of the anterior surface of the lamina cribrosa with respect to the reference plane, a mean of differences between each of the points on the anterior surface of the lamina cribrosa and corresponding points on a smooth curve approximation of the anterior surface of the lamina cribrosa, a standard deviation of the differences, a mean of line curvatures of lines that cross between the anterior surface of the lamina cribrosa and a vertical plane, a standard deviation of the line curvatures, a three-dimensional area of the anterior surface of the lamina cribrosa, a two-dimensional area of a two-dimensional projection onto the reference plane of the anterior surface of the laminal cribrosa, and a ratio of the three-dimensional area to the two-dimensional area.

In the medical diagnostic apparatus the medical condition may be glaucoma; the processor may identify a reference plane maximally correlated with a largest surface of a Bruch's Membrane Opening in the subject's eye; and the at least one diagnostic metric may include at least one of a depth of a lowest point on an anterior surface of a lamina cribrosa in the subject's eye that is furthest from the reference plane, a depth of a highest point on the anterior surface of the lamina cribrosa that is closest to the reference plane, an X coordinate of the lowest point in an X/Y coordinate system of an optical coherence tomography scanner that generates the three-dimensional data, a Y coordinate of the lowest point in the X/Y coordinate system, an X coordinate of the highest point in the X/Y coordinate system, a Y coordinate of the highest point in the X/Y coordinate system, a volume of a space between the reference plane and the anterior surface of the lamina cribrosa, an area of a contour of the Bruch's Membrane Opening projected to the reference plane, an average depth of points on the anterior surface of the anterior surface of the lamina cribrosa with respect to the reference plane, a mean of differences between each of the points on the anterior surface of the lamina cribrosa and corresponding points on a smooth curve approximation of the anterior surface of the lamina cribrosa, a standard deviation of the differences, a mean of line curvatures of lines that cross between the anterior surface of the lamina cribrosa and a vertical plane, a standard deviation of the line curvatures, a three-dimensional area of the anterior surface of the lamina cribrosa, a two-dimensional area of a two-dimensional projection onto the reference plane of the anterior surface of the laminal cribrosa, and a ratio of the three-dimensional area to the two-dimensional area.

In the medical diagnostic apparatus the medical condition may be glaucoma; the processor may to identify a reference plane maximally correlated with a largest surface of a Bruch's Membrane Opening in the subject's eye; and the at least one diagnostic metric may include at least two of a depth of a lowest point on an anterior surface of a lamina cribrosa in the subject's eye that is furthest from the reference plane, a depth of a highest point on the anterior surface of the lamina cribrosa that is closest to the reference plane, an X coordinate of the lowest point in an X/Y coordinate system of an optical coherence tomography scanner that generates the three-dimensional data, a Y coordinate of the lowest point in the X/Y coordinate system, an X coordinate of the highest point in the X/Y coordinate system, a Y coordinate of the highest point in the X/Y coordinate system, a volume of a space between the reference plane and the anterior surface of the lamina cribrosa, an area of a contour of the Bruch's Membrane Opening projected to the reference plane, an average depth of points on the anterior surface of the anterior surface of the lamina cribrosa with respect to the reference plane, a mean of differences between each of the points on the anterior surface of the lamina cribrosa and corresponding points on a smooth curve approximation of the anterior surface of the lamina cribrosa, a standard deviation of the differences, a mean of line curvatures of lines that cross between the anterior surface of the lamina cribrosa and a vertical plane, a standard deviation of the line curvatures, a three-dimensional area of the anterior surface of the lamina cribrosa, a two-dimensional area of a two-dimensional projection onto the reference plane of the anterior surface of the laminal cribrosa, and a ratio of the three-dimensional area to the two-dimensional area.

In the medical diagnostic apparatus the medical condition may be glaucoma; the processor may identify a reference plane maximally correlated with a largest surface of a Bruch's Membrane Opening in the subject's eye; and the at least one diagnostic metric may include at least three of a depth of a lowest point on an anterior surface of a lamina cribrosa in the subject's eye that is furthest from the reference plane, a depth of a highest point on the anterior surface of the lamina cribrosa that is closest to the reference plane, an X coordinate of the lowest point in an X/Y coordinate system of an optical coherence tomography scanner that generates the three-dimensional data, a Y coordinate of the lowest point in the X/Y coordinate system, an X coordinate of the highest point in the X/Y coordinate system, a Y coordinate of the highest point in the X/Y coordinate system, a volume of a space between the reference plane and the anterior surface of the lamina cribrosa, an area of a contour of the Bruch's Membrane Opening projected to the reference plane, an average depth of points on the anterior surface of the anterior surface of the lamina cribrosa with respect to the reference plane, a mean of differences between each of the points on the anterior surface of the lamina cribrosa and corresponding points on a smooth curve approximation of the anterior surface of the lamina cribrosa, a standard deviation of the differences, a mean of line curvatures of lines that cross between the anterior surface of the lamina cribrosa and a vertical plane, a standard deviation of the line curvatures, a three-dimensional area of the anterior surface of the lamina cribrosa, a two-dimensional area of a two-dimensional projection onto the reference plane of the anterior surface of the laminal cribrosa, and a ratio of the three-dimensional area to the two-dimensional area.

In the medical diagnostic apparatus the medical condition may be glaucoma; the processor may identify a reference plane maximally correlated with a largest surface of a Bruch's Membrane Opening in the subject's eye; and the at least one diagnostic metric may include at least four of a depth of a lowest point on an anterior surface of a lamina cribrosa in the subject's eye that is furthest from the reference plane, a depth of a highest point on the anterior surface of the lamina cribrosa that is closest to the reference plane, an X coordinate of the lowest point in an X/Y coordinate system of an optical coherence tomography scanner that generates the three-dimensional data, a Y coordinate of the lowest point in the X/Y coordinate system, an X coordinate of the highest point in the X/Y coordinate system, a Y coordinate of the highest point in the X/Y coordinate system, a volume of a space between the reference plane and the anterior surface of the lamina cribrosa, an area of a contour of the Bruch's Membrane Opening projected to the reference plane, an average depth of points on the anterior surface of the anterior surface of the lamina cribrosa with respect to the reference plane, a mean of differences between each of the points on the anterior surface of the lamina cribrosa and corresponding points on a smooth curve approximation of the anterior surface of the lamina cribrosa, a standard deviation of the differences, a mean of line curvatures of lines that cross between the anterior surface of the lamina cribrosa and a vertical plane, a standard deviation of the line curvatures, a three-dimensional area of the anterior surface of the lamina cribrosa, a two-dimensional area of a two-dimensional projection onto the reference plane of the anterior surface of the laminal cribrosa, and a ratio of the three-dimensional area to the two-dimensional area.

In the medical diagnostic apparatus the medical condition may be glaucoma; the processor may identify a reference plane maximally correlated with a largest surface of a Bruch's Membrane Opening in the subject's eye; and the at least one diagnostic metric includes at least five of a depth of a lowest point on an anterior surface of a lamina cribrosa in the subject's eye that is furthest from the reference plane, a depth of a highest point on the anterior surface of the lamina cribrosa that is closest to the reference plane, an X coordinate of the lowest point in an X/Y coordinate system of an optical coherence tomography scanner that generates the three-dimensional data, a Y coordinate of the lowest point in the X/Y coordinate system, an X coordinate of the highest point in the X/Y coordinate system, a Y coordinate of the highest point in the X/Y coordinate system, a volume of a space between the reference plane and the anterior surface of the lamina cribrosa, an area of a contour of the Bruch's Membrane Opening projected to the reference plane, an average depth of points on the anterior surface of the anterior surface of the lamina cribrosa with respect to the reference plane, a mean of differences between each of the points on the anterior surface of the lamina cribrosa and corresponding points on a smooth curve approximation of the anterior surface of the lamina cribrosa, a standard deviation of the differences, a mean of line curvatures of lines that cross between the anterior surface of the lamina cribrosa and a vertical plane, a standard deviation of the line curvatures, a three-dimensional area of the anterior surface of the lamina cribrosa, a two-dimensional area of a two-dimensional projection onto the reference plane of the anterior surface of the laminal cribrosa, and a ratio of the three-dimensional area to the two-dimensional area.

In the medical diagnostic apparatus the medical condition may be glaucoma; the processor may identify a reference plane maximally correlated with a largest surface of a Bruch's Membrane Opening in the subject's eye; and the at least one diagnostic metric may include at least six of a depth of a lowest point on an anterior surface of a lamina cribrosa in the subject's eye that is furthest from the reference plane, a depth of a highest point on the anterior surface of the lamina cribrosa that is closest to the reference plane, an X coordinate of the lowest point in an X/Y coordinate system of an optical coherence tomography scanner that generates the three-dimensional data, a Y coordinate of the lowest point in the X/Y coordinate system, an X coordinate of the highest point in the X/Y coordinate system, a Y coordinate of the highest point in the X/Y coordinate system, a volume of a space between the reference plane and the anterior surface of the lamina cribrosa, an area of a contour of the Bruch's Membrane Opening projected to the reference plane, an average depth of points on the anterior surface of the anterior surface of the lamina cribrosa with respect to the reference plane, a mean of differences between each of the points on the anterior surface of the lamina cribrosa and corresponding points on a smooth curve approximation of the anterior surface of the lamina cribrosa, a standard deviation of the differences, a mean of line curvatures of lines that cross between the anterior surface of the lamina cribrosa and a vertical plane, a standard deviation of the line curvatures, a three-dimensional area of the anterior surface of the lamina cribrosa, a two-dimensional area of a two-dimensional projection onto the reference plane of the anterior surface of the laminal cribrosa, and a ratio of the three-dimensional area to the two-dimensional area.

In the medical diagnostic apparatus the medical condition may be glaucoma; the processor may identify a reference plane maximally correlated with a largest surface of a Bruch's Membrane Opening in the subject's eye; and the at least one diagnostic metric may include each of a depth of a lowest point on an anterior surface of a lamina cribrosa in the subject's eye that is furthest from the reference plane, an X coordinate of the lowest point in an X/Y coordinate system of an optical coherence tomography scanner that generates the three-dimensional data, a Y coordinate of the lowest point in the X/Y coordinate system, a volume of a space between the reference plane and the anterior surface of the lamina cribrosa, a mean of differences between each of the points on the anterior surface of the lamina cribrosa and corresponding points on a smooth curve approximation of the anterior surface of the lamina cribrosa, a mean of line curvatures of lines that cross between the anterior surface of the lamina cribrosa and a vertical plane, and a ratio of a three-dimensional area of the anterior surface of the lamina cribrosa to a two-dimensional area of a two-dimensional projection onto the reference plane of the anterior surface of the laminal cribrosa.

In the medical diagnostic apparatus the medical condition may be glaucoma; the processor may identify a reference plane maximally correlated with a largest surface of a Bruch's Membrane Opening in the subject's eye; and the at least one diagnostic metric may include each of a depth of a lowest point on an anterior surface of a lamina cribrosa in the subject's eye that is furthest from the reference plane, a depth of a highest point on the anterior surface of the lamina cribrosa that is closest to the reference plane, an X coordinate of the lowest point in an X/Y coordinate system of an optical coherence tomography scanner that generates the three-dimensional data, a Y coordinate of the lowest point in the X/Y coordinate system, an X coordinate of the highest point in the X/Y coordinate system, a Y coordinate of the highest point in the X/Y coordinate system, a volume of a space between the reference plane and the anterior surface of the lamina cribrosa, an area of a contour of the Bruch's Membrane Opening projected to the reference plane, an average depth of points on the anterior surface of the anterior surface of the lamina cribrosa with respect to the reference plane, a mean of differences between each of the points on the anterior surface of the lamina cribrosa and corresponding points on a smooth curve approximation of the anterior surface of the lamina cribrosa, a standard deviation of the differences, a mean of line curvatures of lines that cross between the anterior surface of the lamina cribrosa and a vertical plane, a standard deviation of the line curvatures, a three-dimensional area of the anterior surface of the lamina cribrosa, a two-dimensional area of a two-dimensional projection onto the reference plane of the anterior surface of the laminal cribrosa, and a ratio of the three-dimensional area to the two-dimensional area.

In the medical diagnostic apparatus the medical condition may be an ocular or non-occular neuropathy; the ocular neuropathy may include at least one of ischemic neuropathy, traumatic neuropathy, genetic neuropathy, inflammatory neuropathy, drug-induced neuropathy, congenital neuropathy, and pathologic myopia neuropathy; the non-ocular neuropathy may include at least one of a brain tumor, intracerebral hemorrhage, brain trauma, brain abscess, meningitis, encephalitis, pseudotumor cerebri, a cerebrovascular disorder, and hypertension; the processor may evaluate a progress or a risk of the ocular or non-occular neuropathy based on the at least one diagnostic metric including at least one of a depth of a lowest point on an anterior surface of a lamina cribrosa in the subject's eye that is furthest from the reference plane, a depth of a highest point on the anterior surface of the lamina cribrosa that is closest to the reference plane, an X coordinate of the lowest point in an X/Y coordinate system of an optical coherence tomography scanner that generates the three-dimensional data, a Y coordinate of the lowest point in the X/Y coordinate system, an X coordinate of the highest point in the X/Y coordinate system, a Y coordinate of the highest point in the X/Y coordinate system, a volume of a space between the reference plane and the anterior surface of the lamina cribrosa, an area of a contour of the Bruch's Membrane Opening projected to the reference plane, an average depth of points on the anterior surface of the anterior surface of the lamina cribrosa with respect to the reference plane, a mean of differences between each of the points on the anterior surface of the lamina cribrosa and corresponding points on a smooth curve approximation of the anterior surface of the lamina cribrosa, a standard deviation of the differences, a mean of line curvatures of lines that cross between the anterior surface of the lamina cribrosa and a vertical plane, a standard deviation of the line curvatures, a three-dimensional area of the anterior surface of the lamina cribrosa, a two-dimensional area of a two-dimensional projection onto the reference plane of the anterior surface of the laminal cribrosa, and a ratio of the three-dimensional area to the two-dimensional area.

In the medical diagnostic apparatus the medical condition may be an ocular or non-occular neuropathy; the ocular neuropathy may include at least one of ischemic neuropathy, traumatic neuropathy, genetic neuropathy, inflammatory neuropathy, drug-induced neuropathy, congenital neuropathy, and pathologic myopia neuropathy; the non-ocular neuropathy may include at least one of a brain tumor, intracerebral hemorrhage, brain trauma, brain abscess, meningitis, encephalitis, pseudotumor cerebri, a cerebrovascular disorder, and hypertension; the processor may evaluate a progress or a risk of the ocular or non-occular neuropathy based on the at least one diagnostic metric including each of a depth of a lowest point on an anterior surface of a lamina cribrosa in the subject's eye that is furthest from the reference plane, an X coordinate of the lowest point in an X/Y coordinate system of an optical coherence tomography scanner that generates the three-dimensional data, a Y coordinate of the lowest point in the X/Y coordinate system, a volume of a space between the reference plane and the anterior surface of the lamina cribrosa, a mean of differences between each of the points on the anterior surface of the lamina cribrosa and corresponding points on a smooth curve approximation of the anterior surface of the lamina cribrosa, a mean of line curvatures of lines that cross between the anterior surface of the lamina cribrosa and a vertical plane, and a ratio of a three-dimensional area of the anterior surface of the lamina cribrosa to a two-dimensional area of a two-dimensional projection onto the reference plane of the anterior surface of the laminal cribrosa.

In the medical diagnostic apparatus the medical condition may be an ocular or non-occular neuropathy; the ocular neuropathy may include at least one of ischemic neuropathy, traumatic neuropathy, genetic neuropathy, inflammatory neuropathy, drug-induced neuropathy, congenital neuropathy, and pathologic myopia neuropathy; the non-ocular neuropathy may include at least one of a brain tumor, intracerebral hemorrhage, brain trauma, brain abscess, meningitis, encephalitis, pseudotumor cerebri, a cerebrovascular disorder, and hypertension; the processor may evaluate a progress or a risk of the ocular or non-occular neuropathy based on the at least one diagnostic metric including each of a depth of a lowest point on an anterior surface of a lamina cribrosa in the subject's eye that is furthest from the reference plane, a depth of a highest point on the anterior surface of the lamina cribrosa that is closest to the reference plane, an X coordinate of the lowest point in an X/Y coordinate system of an optical coherence tomography scanner that generates the three-dimensional data, a Y coordinate of the lowest point in the X/Y coordinate system, an X coordinate of the highest point in the X/Y coordinate system, a Y coordinate of the highest point in the X/Y coordinate system, a volume of a space between the reference plane and the anterior surface of the lamina cribrosa, an area of a contour of the Bruch's Membrane Opening projected to the reference plane, an average depth of points on the anterior surface of the anterior surface of the lamina cribrosa with respect to the reference plane, a mean of differences between each of the points on the anterior surface of the lamina cribrosa and corresponding points on a smooth curve approximation of the anterior surface of the lamina cribrosa, a standard deviation of the differences, a mean of line curvatures of lines that cross between the anterior surface of the lamina cribrosa and a vertical plane, a standard deviation of the line curvatures, a three-dimensional area of the anterior surface of the lamina cribrosa, a two-dimensional area of a two-dimensional projection onto the reference plane of the anterior surface of the laminal cribrosa, and a ratio of the three-dimensional area to the two-dimensional area.

An embodiment of the invention may include a method of medical diagnosis including obtaining three-dimensional data of a subject's eye; separating portions of the three-dimensional data into separate segments; performing processing differently on each of the separate segments; combining the separately processed segments to produce a segmented three-dimensional data set; generating at least one diagnostic metric from the segmented three-dimensional data set; and evaluating a medical condition based on the at least one diagnostic metric.

An embodiment of the invention may include a non-tangible, computer readable medium storing instructions, which when executed by a computer, performs steps that include obtaining three-dimensional data of a subject's eye; separating portions of the three-dimensional data into separate segments; performing processing differently on each of the separate segments; combining the separately processed segments to produce a segmented three-dimensional data set; generating at least one diagnostic metric from the segmented three-dimensional data set; and evaluating a medical condition based on the at least one diagnostic metric.

BRIEF DESCRIPTION OF THE DRAWINGS

The scope of the present disclosure is best understood from the following detailed description of exemplary embodiments when read in conjunction with the accompanying drawings, wherein:

FIG. 4 is a list of metrics extracted and analyzed by an embodiment of the invention.

DETAILED DESCRIPTION

Figure 1:
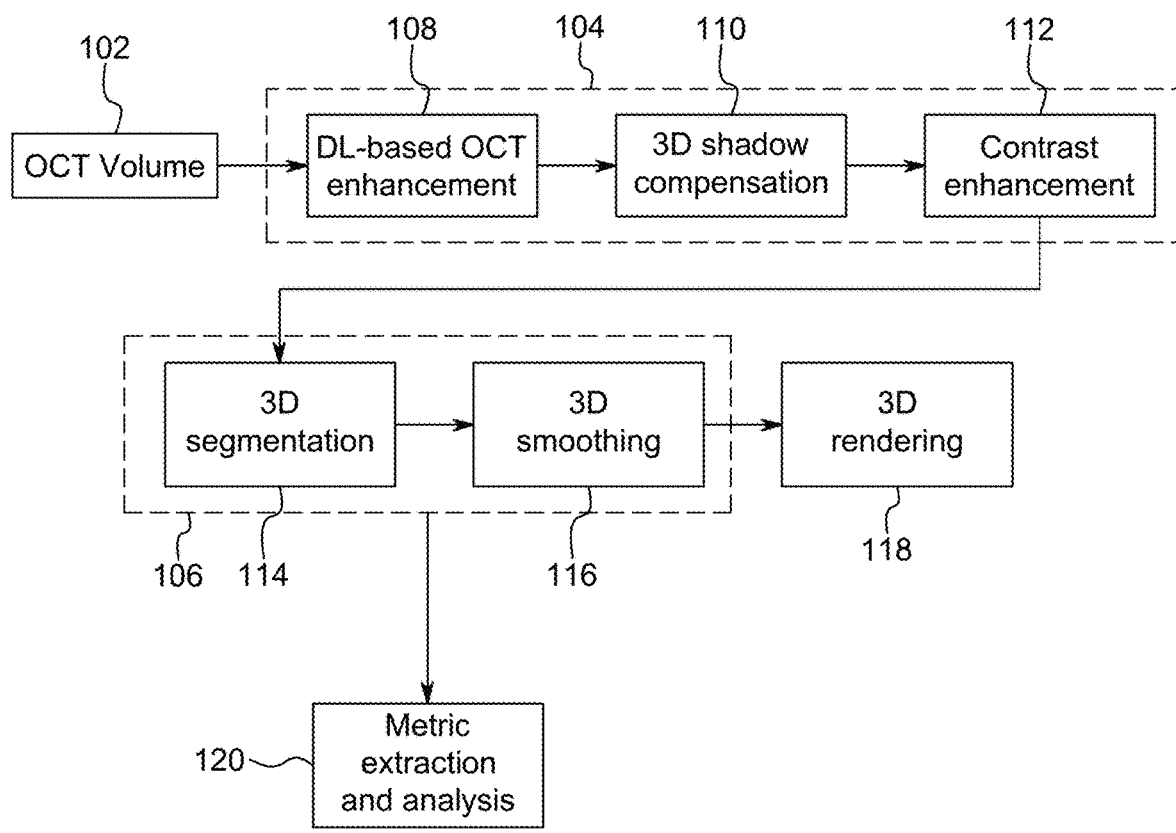
FIG. 1 illustrates an embodiment of the invention.

Evidence suggests that the optic nerve head (ONH) may be a principal site at which the retinal nerve fibers (optic nerve axons) are damaged in glaucoma. The ONH is the most anterior part of the optic nerve where retinal nerve fibers exit from the eyeball. In particular, morphological changes and damages of the lamina cribrosa (LC), a sieve-like structure in the ONH that lends support to retinal nerve fibers, are the hallmarks of glaucoma in histological studies. However, it has previously been difficult to obtain high resolution imagery of the LC.

Although evidence suggests that the LC is a principal site of axonal insult in glaucoma, and previous work has reported changes of the LC from glaucoma, previous studies have not been able to capture sufficient detail regarding the complex shape of the LC. An embodiment of the invention may perform clinically valuable analyses and visualizations of three-dimensional (3D) OCT data that was not previously practical and/or possible with known technologies. Such analyses and visualizations may improve a medical practitioner's ability to diagnose disease, monitor, and manage treatment (i.e., evaluate progress or risk of a pathological condition). Briefly, the analysis is performed on, and the visualizations are created by, segmenting OCT data for a component of interest (e.g., the LC) in three dimensions following a series of pre-processing techniques. The segmentation can be applied to the data following pre-processing, and then combined to produce a final full 3D segmentation of the desired component. Post-processing, such as a smoothing technique, may be then applied to the segmented component.

The eye is the most important sensory organ and the window to observe the general health of the body. With the recent advancements in high speed and noninvasive eye imaging incorporated with optical coherence tomography (OCT), more health-related information can be revealed through the imaging of eye. As a portal between the eye and surrounding tissue, the LC is sensitive to changes in eye pressure. An embodiment of the present invention improves the ability to consider the LC structure in 3D uses deep-learning-based, automatic 3D LC visualization and measurement of OCT images.

The embodiments enable high sensitivity and specificity in diagnosing diseases that may cause changes to the LC structure, such as increased depth, increased curvature, and the development of focal defects. These morphological characteristics may be used as structural biomarkers of disease, such as glaucoma. Further, evaluation of these LC characteristics in 3D allows for evaluation of structural changes that are not evident from analysis of only 2D structures, such as depth or cross-sectional curvature.

An embodiment of the invention may visualize and quantify LC structure using novel image processing that extracts the 3D information from the OCT image volumes. In this method, a series of pre-processing techniques are employed to address the issues that adversely influence the OCT image quality and thus the quantification. These include the speckle and random noises, shadow artifacts, and the signal attenuation and reduced image contrast in deep layers. Notably, the present pre-processing method works on a single OCT volume (e.g., a volume captured from a single OCT scan) that is routinely acquired without specific acquisition protocols, offering a practical advantage that it can be applied retrospectively to the existing database to get new insights of the disease conditions. The LC structure is then segmented sequentially from the pre-processed OCT volume by an embodiment of the invention using a deep-learning-based algorithm.

An example method for producing clinically valuable analyses and visualizations according to the present disclosure is illustrated in FIG. 1. As seen therein, a receiver 102 is configured to acquire or otherwise receive raw 3D OCT data either by performing an OCT scan or by retrieving results from a previously performed OCT scan. The acquired data may then undergo pre-processing 104 (including deep learning (DL) based OCT enhancement 108, 3D shadow compensation 110, and contrast enhancement 112) and segmentation 106 (including 3D segmentation 114 and 3D smoothing 116). The segmented 3D data that results from the 3D smoothing 116 may be used to create 3D images by 3D rendering 118 and/or may be further processed for metric extraction and analysis 120. The pre-processing 104, segmentations 106, 3D rendering 118, and metric extraction and analysis 120 are performed by a processing circuit programmed to perform the required functions described herein. The processing circuit may include application specific hardware and circuits and/or programmed processor circuits (e.g., microprocessor, CPU, computer, etc . . . ) as discussed further below.

The pre-processing 104 may, for example, address speckle and other noise in the data and images by applying a deep-learning based noise reduction technique, such as that described in U.S. patent application Ser. No. 16/797,848, filed Feb. 21, 2020 and titled "Image Quality Improvement Methods for Optical Coherence Tomography," the entirety of which is herein incorporated by reference. Further, shadow and projection artifacts may be reduced by applying image-processing and/or deep-learning techniques, such as that described in U.S. patent application Ser. No. 16/574,453, filed Sep. 28, 2019 and titled "3D Shadow Reduction Signal Processing Method for Optical Coherence Tomography (OCT) Images," the entirety of which is herein incorporated by reference. Of course, other de-noising techniques may be applied.

The pre-processing 104 may be applied to entire raw images or volumes, or only selected regions of interest. As a result, for each raw image or volume input to the pre-processing 104, multiple pre-processed images may be produced. Put another way, individual B-scans or C-scans taken from raw three-dimensional OCT data may be subject to different pre-processing techniques to produce multiple pre-processed images. Following pre-processing 104, the pre-processed images (or data underlying the images) are segmented 114 and 3D smoothed 116 for a desired component in the images/data, such as the anterior of the LC. The 3D segmentation process 114 may utilize one or more different techniques, where each applied segmentation technique may individually be relatively simple and fast to perform and have different strengths and weaknesses.

Some segmentation techniques 114 may be applied on the original image frames (after pre-processing enhancement). Some other segmentation techniques 114 may be applied on the original frames enhanced by neighboring frames (e.g., weighted average). Some other segmentation techniques 114 may be applied on interpolated radial frames passing through the disc center to ensure each frame has a significant region with LC and not just include the LC border. Segmentation techniques can be conventional edge-detection-based or graph-cut-based segmentation techniques or deep learning based segmentation techniques.

In view of the above, the different segmentation techniques can be selectively applied to one or more of the pre-processed images. Further, segmentation of the LC anterior surface has not previously been practically possible in 3D OCT volume due to noise and attenuation (e.g., causing artifacts). However, following application of the above-described pre-processing, the segmentation techniques may also be applied to entire OCT volumes according to an embodiment of the invention, rather than in averaged line-scans or radial scans.

In one embodiment of the invention, each segmentation technique may be applied to images/data having been separately pre-processed. In another embodiment, segmentation techniques may be selectively applied to images/data corresponding to different regions of interest. For example, a first of two pre-processed images may be segmented according to a first segmentation technique, while a second of the two pre-processed images may be segmented according a second segmentation technique.

Regardless of the number of pre-processing and segmentation techniques applied, the segmentations are then combined to produce a composite/enhanced segmented image or data, which accurately reflects the structure of the anterior LC surface and of sufficient quality for processing to determine different quantitative metrics 120 as part of an analysis and visualization of the segmentation and/or the metrics (e.g., diagnostic metrics).

In the 3D segmentation 114, the Bruch's Membrane Opening (BMO) may be detected first before the LC segmentation. The BMO is used by an embodiment of the invention to indicate a boundary of the LC anterior surface segment and thereby bound the segmentation of the LC anterior surface. As discussed further below, a BMO contour 212 is identified in the data. The 3D segmentation 114 generates a plane fitted to the BMO contour 212, which is a locus of points along the perimeter of the Bruch's Membrane, and the plane is used as a reference against which different parameters are extracted and calculated to provide the bases for diagnostic metrics.

Figure 3:
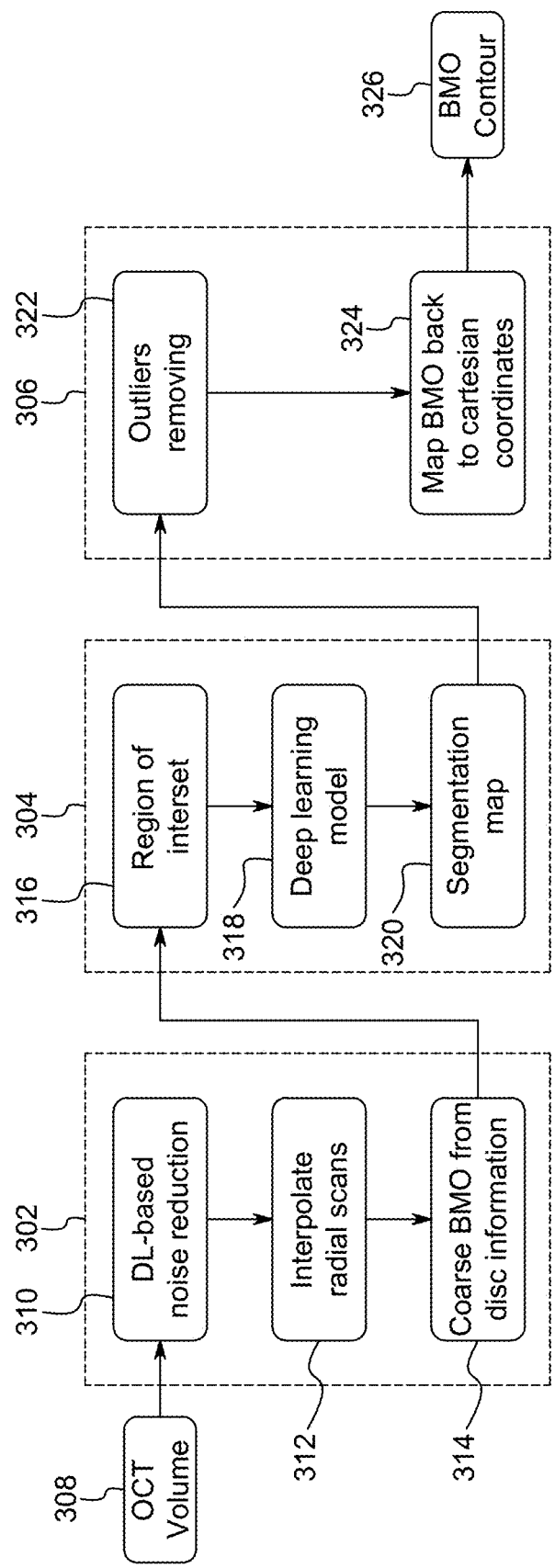
FIG. 3 shows an embodiment of the BMO segmentation process according to an embodiment of the invention.

FIG. 3 shows an embodiment of the invention including pre-processing 302, DL-based detection 304, and post-processing 306. A rough disc region of the eye is segmented on the OCT enface image based on image intensity. The disc center is detected and resampled by scans made radially across the disc center. Each image may be cropped using a rough disc segmentation as a seed (center). Then, a DL algorithm (which is trained from manual labels) is applied to the cropped image to detect BMO. Additional processing is performed in 3D to remove outlier data points and convert the BMO points back to Cartesian coordinates to obtain a BMO contour 326.

Figure 2:
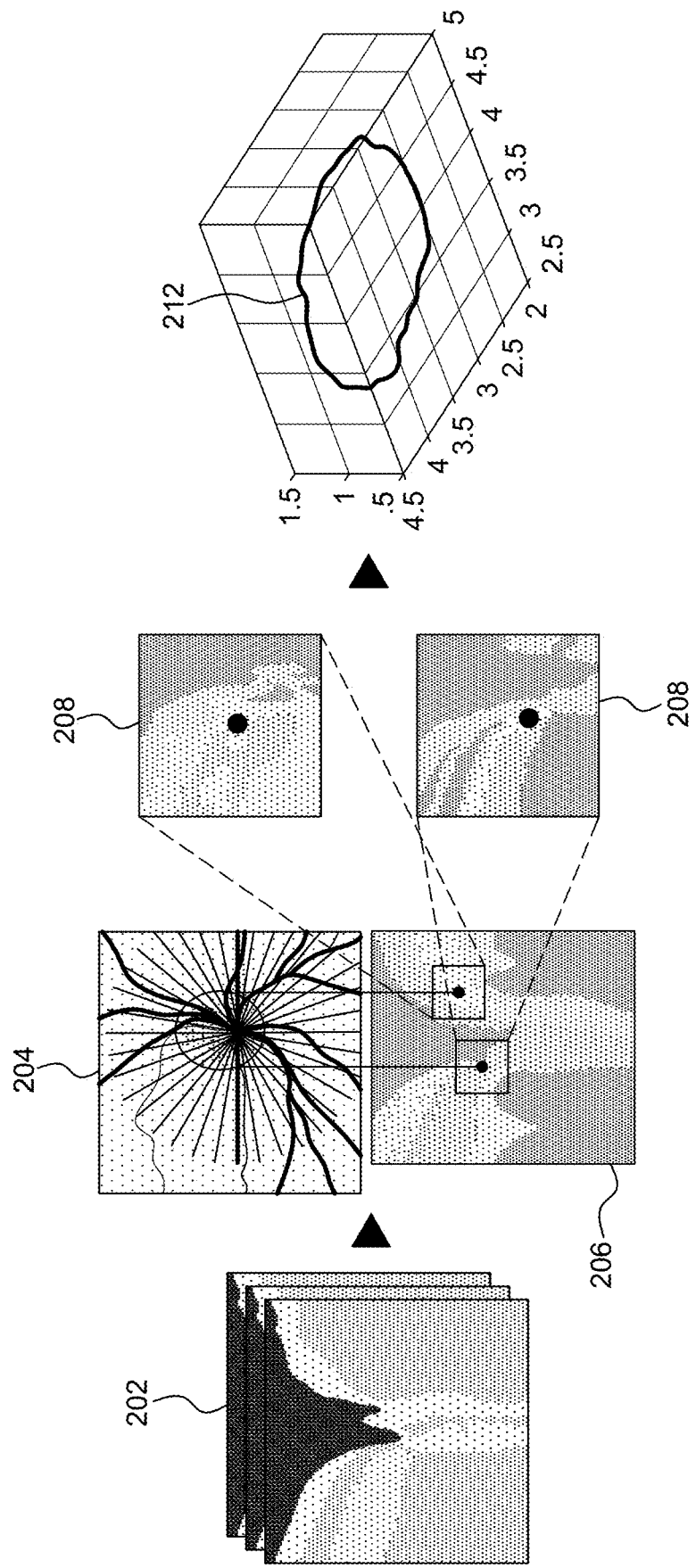
FIG. 2 shows exemplary 2D and 3D visualizations produced by an embodiment of the invention.

FIG. 2 shows exemplary 2D and 3D visualizations produced by an embodiment of the invention.

FIG. 3 shows an embodiment of the BMO segmentation process with. The acquired raw OCT volume (202, 308) is first pre-processed 302 with DL-based noise reduction 310, resampled radially across the disc center (204, 312), and coarse BMO segmentation 314 is performed with OCT enface image based on image intensity. BMO segmentation step 304 consists of cropping each image using a rough disc segmentation as a seed (center) (316, 206). Then, a DL algorithm 318 (which is trained from manual labels) is applied to the cropped image (208) to detect BMO. An initial segmentation map 320 is obtained and post-processing 306 is applied including outlier removal 322 and mapping detected points back to Cartesian coordinates 324. A final BMO contour (326, 212) is obtained after the processing.

The segmented surface may be processed to generate and analyze quantifiable metrics based on the three-dimensional OCT data. Because these diagnostic metrics (also referred to interchangeably as parameters and metrics, herein) are generated from the above-described pre-processed and segmented enhanced OCT data, the metrics are significantly more accurate than metrics derived from OCT data according to traditional techniques. Further, the metrics (and any visualizations generated from the metrics) may be determined within the whole LC region.

FIG. 4 lists metrics extracted and analyzed 120 according to an embodiment of the invention. For example, the metrics include depth measurements and coordinates of lowest and high points on the anterior surface of the LC (Low, High, Lx, Ly, Hx, Hy), volume of the region between the BMO reference plane and the anterior LC surface (Vol), an area of the BMO contour (Bmo), an average depth of the anterior LC surface from the BMO reference plane (Avg_d), mean differences between anterior LC surface with the polynomial best-fitting smooth surface as one measure of anterior LC surface roughness (D_mean), standard deviation of differences between anterior LC surface with the polynomial best-fitting smooth surface as another measure of anterior LC surface roughness (D_std), mean of line curvatures of anterior LC surface as one indication of the anterior LC surface shape (R_mean), standard deviation of line curvatures of anterior LC surface as another indication of the anterior LC surface shape (R_std), 3D surface area of anterior LC surface (Area3), 2D area of anterior LC surface projection on the BMO reference plane (Area2), and a measure of roughness calculated by dividing Area3 by Area2 (Ratio=Area3/Area2). The BMO reference plane 808,906 is calculated by the metric extraction and analysis 120 by finding a plane that most closely matches (i.e., is maximally correlated with) the BMO contour segmented from the OCT volume. The polynomial plane best-fitting smooth surface 704 is calculated by the metric extraction and analysis 120 by finding a best-matching polynomial surface that is maximally correlated with a surface of the segmented LC surface from the segmented OCT data.

These metrics may indicate various conditions related to glaucoma or other neurological disorders. For example, increases in LC depth corresponds to posterior distortions in histologic studies of glaucoma eyes. The location (i.e., coordinates) of LC distortion may correspond to areas with greater damage. LC volume may be interpreted as a sum of posterior LC distortions, and LC curvature may be significantly larger in glaucoma eyes, reflecting the posterior distortion of the LC caused by glaucoma. Location, volume, and roughness are 3D structural parameters that could not have been accurately calculated using conventional 2D methods.

Figure 5:
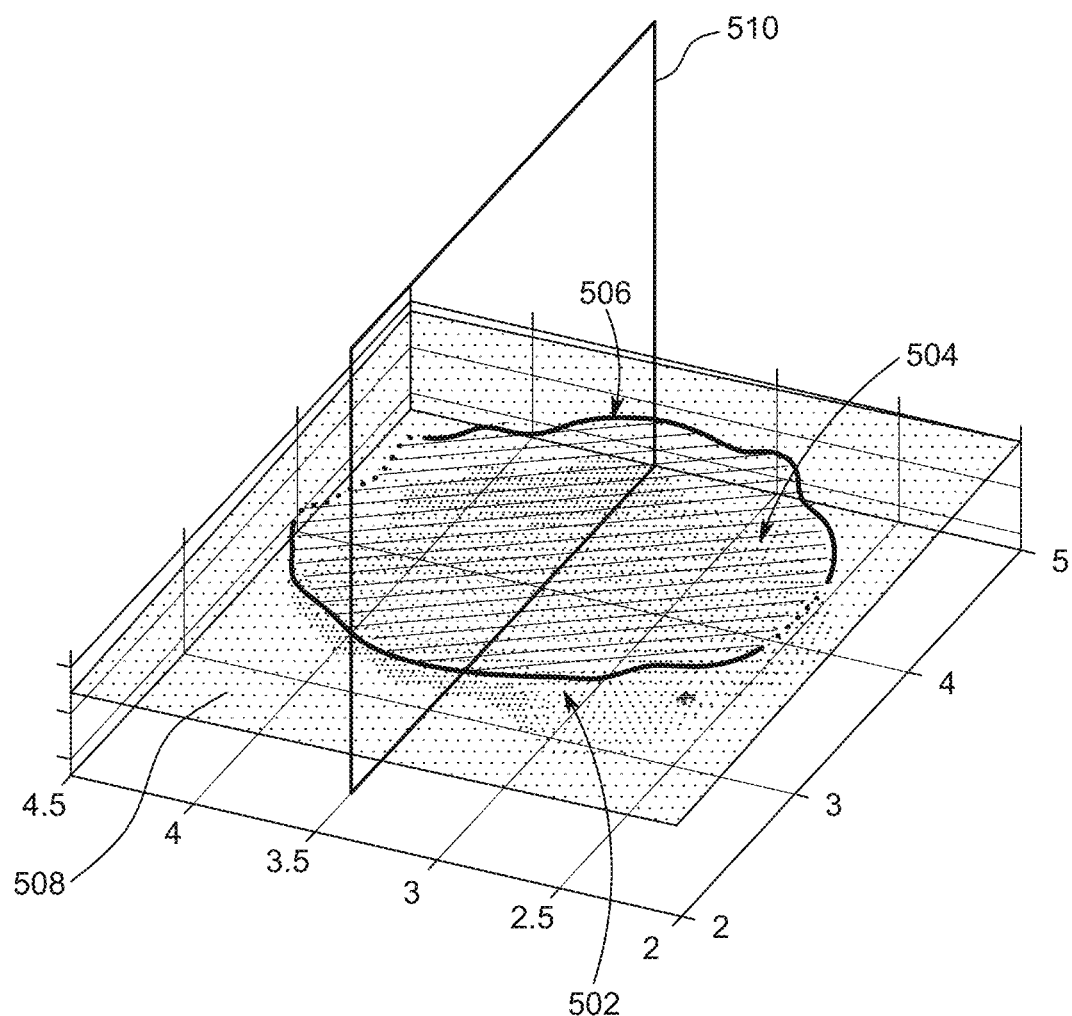
FIG. 5 is an example of structural parameters and metrics extracted by an embodiment of the invention.

FIG. 5 shows an example of structural parameters and metrics extracted from a 3D rendering of an anterior LC surface 502 by an embodiment of the invention. The automatically extracted information includes location of a BMO reference plane 508, a BMO contour 506 and a BMO area 504.

Parameters are extracted with respect to important surfaces and important locations on those surfaces. Important surfaces automatically identified and extracted by an embodiment of the invention include: the segmented anterior LC surface with complex morphology (anterior LC surface for short), a plane fitted to the BMO contour (BMO reference plane), and a smooth paraboloid fitted to the anterior LC surface (fitted paraboloid). Important locations automatically identified and extracted by an embodiment of the invention include: an optic nerve disc center (disc center) obtained by locating the centroid of the BMO contour, and highest/lowest point (with respect to the BMO reference plane): the point on the anterior LC surface that has the largest/smallest distance (perpendicular) to the BMO reference plane.

Parameters are calculated from the 3D data as follows.

Depth of LC: the (perpendicular) distance from each point on the anterior LC surface to the BMO reference plane. Particularly, the depth at the lowest/highest point are important parameters (depth at the lowest/highest point). The average depth for all the points at the anterior LC surface is calculated as the average depth.

X/Y coordinate of the lowest/highest point: the X/Y locations in the scanning coordinates of the lowest/highest points on the anterior LC surface.

Figure 7:
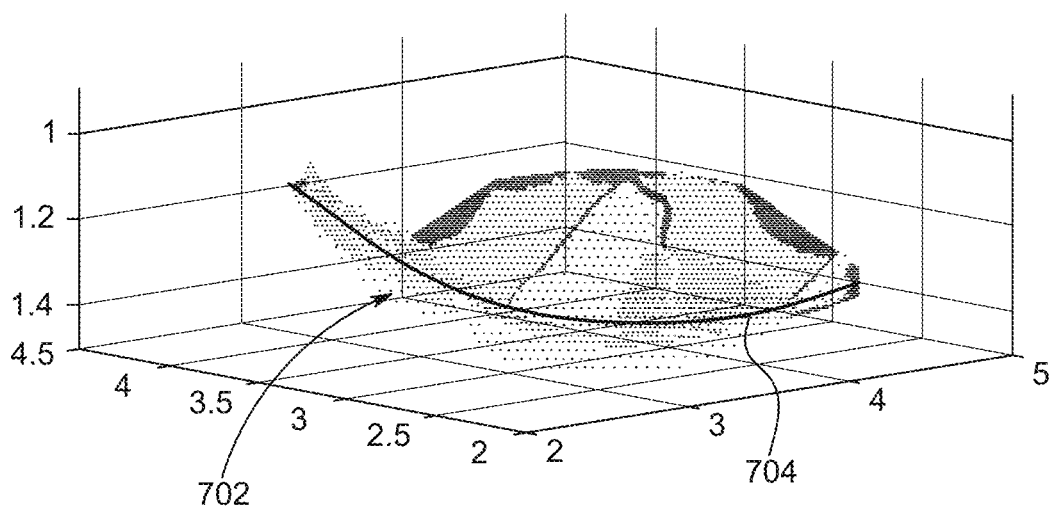
FIG. 7 is another example of structural parameters and metrics extracted by an embodiment of the invention.

Surface distance: as shown in the example of FIG. 7, the distance between the anterior LC surface 702 and the fitted paraboloid 704 at each A-line location. In this extraction, the embodiment first obtains nAlines*nFrames surface distances in total. An OCT scanner can obtain imaging information for all the depths (Z direction) at one point in the XY plane at a time point. An OCT volume is taken in a raster scan pattern in the XY plane. The scan starts from the initial Y position and scans along X direction (aline direction) to complete a frame, each frame has the size nDepth*nAlines. Then the scanner moves to the next Y position or frame position to scan the next frame until all the frames (total of nFrames) have been scanned. The size of the complete OCT volume is nDepth*nAlines*nFrames. Then, the mean (Dist mean) and standard deviation (Dist std) of all the surface distances are calculated as important parameters.

Figure 6:
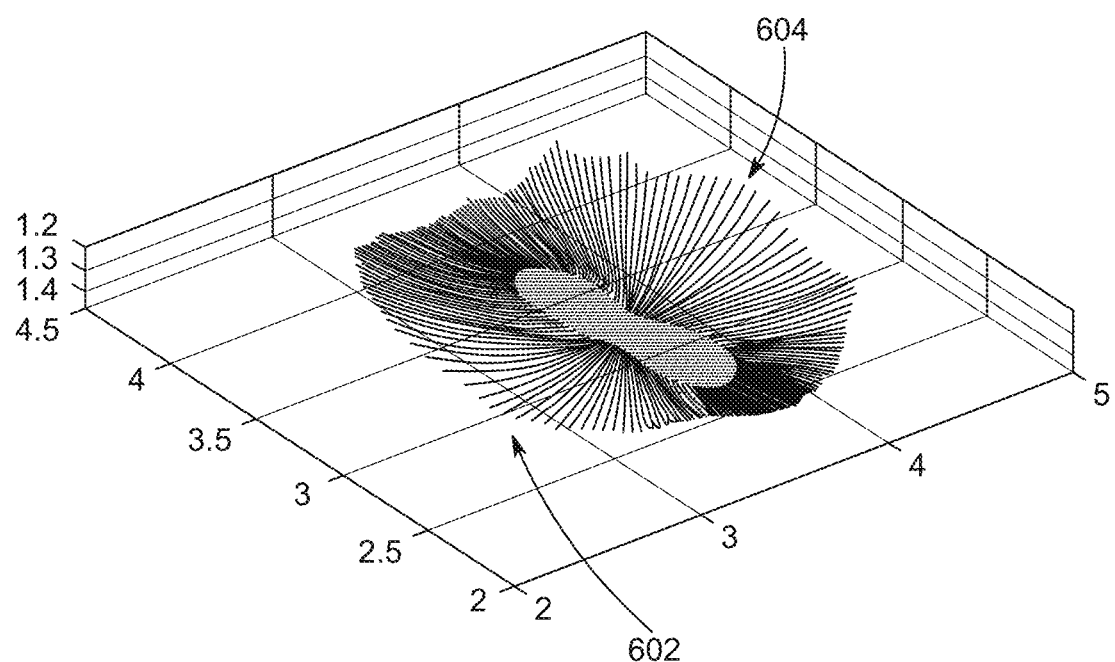
FIG. 6 is another example of structural parameters and metrics extracted by an embodiment of the invention.

Line curvature: within a plane parallel to the Z direction and along each degree angle defined in the XY plane of the scanner coordinate system an embodiment of the invention obtains a crossing line between the anterior LC surface and the vertical (parallel to z/A-line direction) plane passing the disc center, and the curvature for the crossing line at the disc center can be calculated as the line curvature along the angle. The anterior LC surface contour can be sliced by a plane parallel to Z direction and along each degree angle defined in XY plane. The crossing line between the anterior LC and the vertical plane 510 is a curve 604 where an embodiment of the invention can measure the curvature. For example, along each angle (e.g., 1 degree apart), a series (e.g., 180) of line curvatures can be calculated. The average (mean) and the std of the line curvatures are recorded as important parameters. For example, FIG. 6 shows an example of crossing lines 602 that pass through the optic disc center. Curvature of the crossing lines are represented by R_mean and R_std.

BMO area: the surface area of the surface defined by the BMO contour (projected to the BMO reference plane). The BMO contour is a collection of points in 3D, that form a complex curved line. BMO plane is a plane best fitted to the BMO contour. BMO area is the area on the BMO plane defined by projecting the BMO contour perpendicularly onto the BMO plane.

3D area: the surface area of the anterior LC surface.

2D area: the area of the projection of anterior LC surface at the BMO reference plane.

Figure 8:
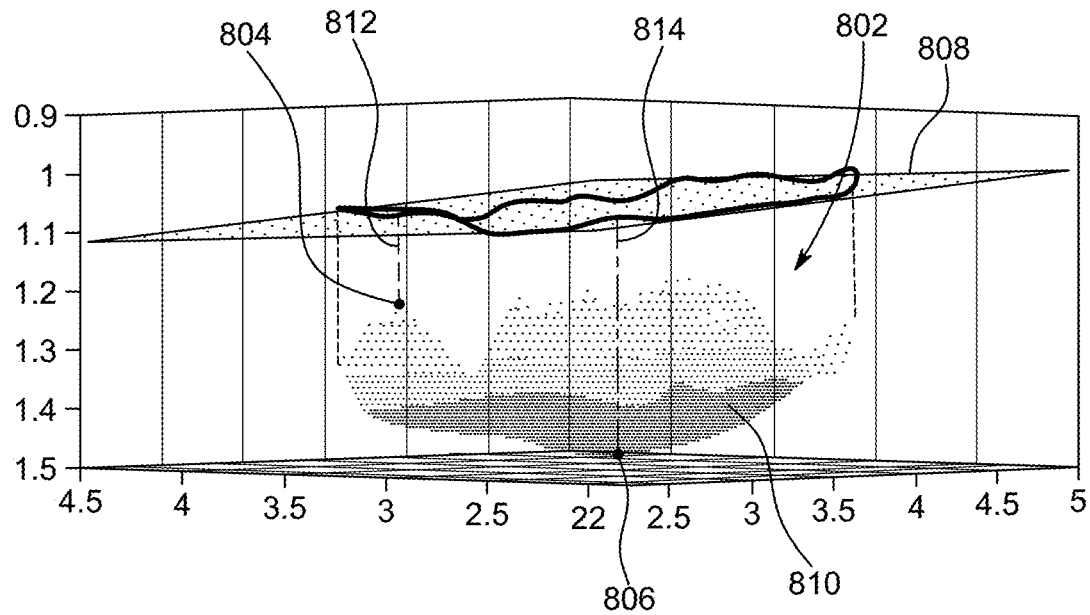
FIG. 8 is another example of structural parameters and metrics extracted by an embodiment of the invention.

Pre-LC volume (Vol): FIG. 8 shows an example of extracting and calculating the volume 802 of the whole region between the anterior LC surface 810 and the BMO reference plane 808, which can be calculated by multiplying the sum of all the depths of LC at each point with the pixel resolution along the BMO reference plane 808. Also illustrated are the height 812 of the highest point 804 and height 814 of the lowest point 806 on the anterior LC surface 810.

Figure 9:
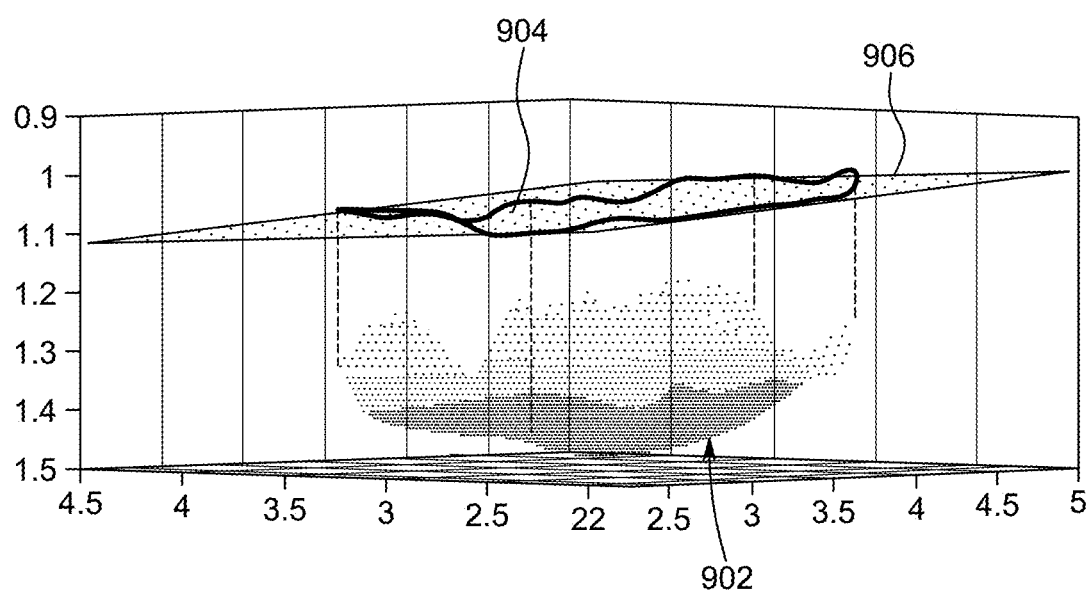
FIG. 9 is another example of structural parameters and metrics extracted by an embodiment of the invention.

Surface area ratio: the ratio between 3D and 2D area (measures the flatness of the surface). As shown in the example of FIG. 9, a surface roughness (Ratio) may be calculated by dividing a 3D surface area 902 (Area3) by a 2D surface area 904 on the BMO reference plane 906 (Area2). Area2 is equivalent to the BMO area.

Based on their clinical experience, the inventors have found that LC morphology is different between glaucoma subjects and normal control subjects. The difference in the morphology can be reflected in the metrics shown in FIG. 4 and discussed above. The metrics can capture morphological changes related with glaucoma and therefore can be used for early detection of glaucoma.

An XGboost machine-learning model was built to integrate the morphological characteristics reflected by the above-mentioned multiple LC metrics to improve the performance for detecting glaucoma. In the dataset, the LC was significantly deeper in glaucoma patients (0.53±0.14 mm) than control subjects (0.47±0.09 mm, P=0.002). The best performing single LC parameter in discriminating glaucoma from control was the depth of the lowest point (AUC 0.64).

The optimized XGBoost analyses yielded excellent discriminating performance (AUC 0.90), which was better than the AUC value of the total RNFL(retinal nerve fiber layer) thickness (0.85). RNFL is one of the sublayers of the retina, consisting of the nerve fibers of the optic nerve. Diseases which cause damages of the optic nerve (collectively called as optic neuropathies) demonstrate thinning of the RNFL. Therefore, thickness of the RNFL is the most commonly used OCT parameter for diagnosing optic neuropathies such as glaucoma.

Figure 10:
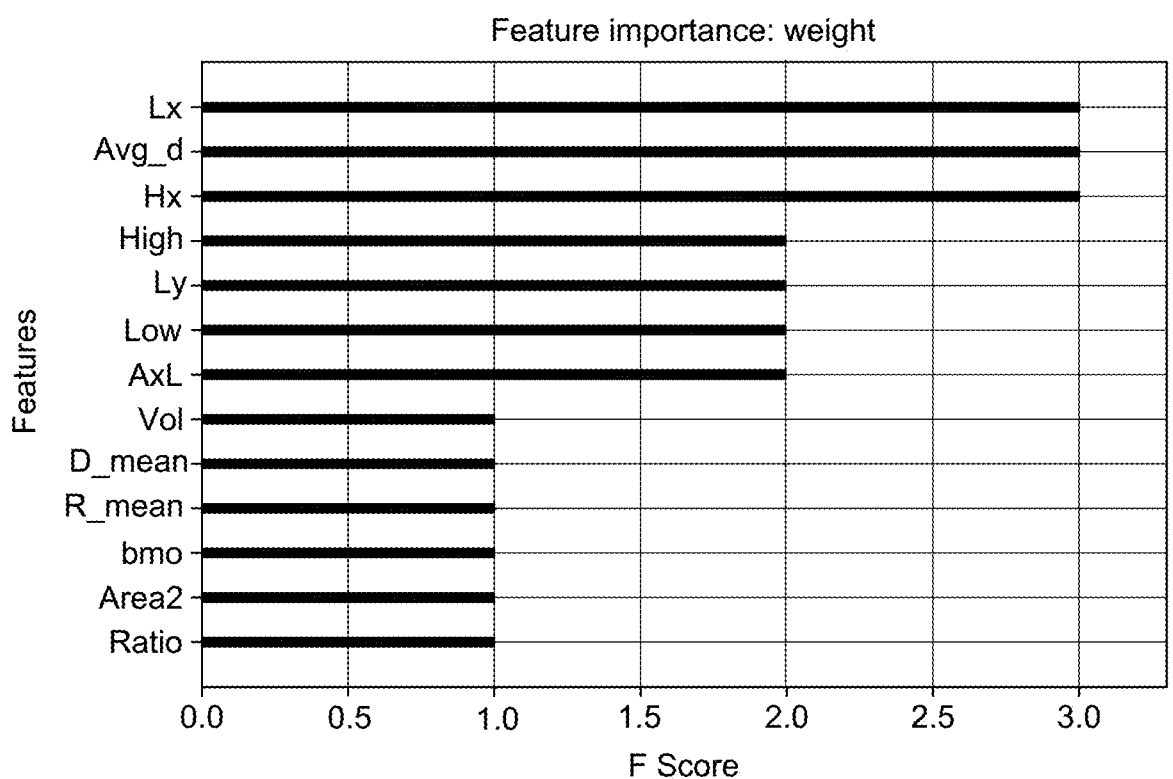
FIG. 10 shows results of an analysis indicating relative weights of metrics extracted by an embodiment of the invention.
Figure 11:
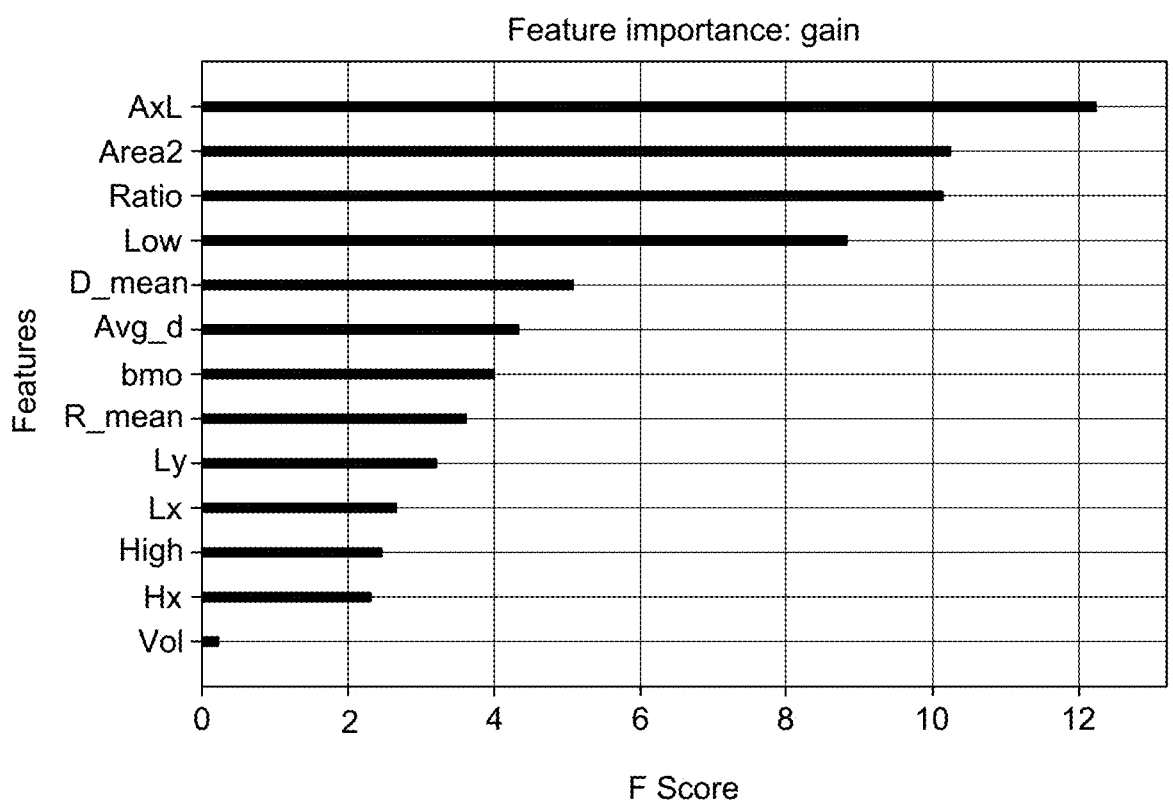
FIG. 11 shows results of an analysis indicating relative gain of metrics extracted by an embodiment of the invention.

Xgboost uses explainable decision tree structure rather than a black-box decision, improving interpretability of the results. FIGS. 10 and 11 show results of the XGBoost analysis indicating the relative importance of the metrics through the weight and gain of each listed feature (metric). In this example, AxL refers to axial length, which is not measured from anterior LC surface but is a standard measurement during routine eye exams. Axial length is the distance from the corneal surface to the Bruch's membrane layer, and it reflects the size of the eye. Axial length is clinically used for evaluating the magnitude of eyeball elongation caused by myopia. Myopia significantly increases the risk of glaucoma because of the abnormal elongation of the eyeball.

The analysis results in FIGS. 10 and 11 show that each of the selected metrics contributes to the final decision. Each of the metrics may be used individual in an embodiment of the invention as factor in glaucoma detection (e.g., one of the metrics shown in FIG. 4). Alternatively, combinations of any two metrics, any three metrics, any four metrics, etc. or all the metrics listed in FIG. 4, can perform as increasingly useful indicators of glaucoma detection. For example, an embodiment of the invention using a combination of only the seven metric subset including Low, Lx, Ly, Vol, D_mean, R_mean, and Ratio provides an effective indication of glaucoma.

An embodiment of the invention can identify occurrence and severity of a target medical condition in a subject based on one or more of the metrics identified in FIG. 4 taken individually, in combination with each other, and/or in combination with conventional RNFL retinal nerve fiber layer parameters. As discussed above, the target medical condition may be glaucoma, the most common type of optic neuropathies. In addition, the target medical condition may include other ocular and non-ocular pathologies. Other ocular pathologies include other optic neuropathies such as ischemic, traumatic, genetic, inflammatory, drug-induced, and congenital neuropathies, and pathologic myopia, which may cause substantial distortion of the ONH (optic nerve head). Moreover, an embodiment of the invention can expand the clinical application of OCT to non-ocular pathologies which are presently not diagnosed using OCT. These non-ocular target pathologies include pathologies which may cause papilledema (i.e., elevation of the ONH caused by increased intracranial pressure) such as brain tumors, intracerebral hemorrhage, brain trauma, brain abscess, meningitis, encephalitis, pseudotumor cerebri, cerebrovascular disorders, and malignant hypertension. An embodiment of the invention may provide an opportunity for applying the ONH imaging to diagnosing pathologies of the central nervous system by leveraging the characteristics of the ONH as a portal between the eye and the central nervous system.

Without the need for special protocols, the techniques used here do not need to be connected directly or simultaneously to an OCT scanner and can be applied retrospectively on any existing 3D data. The 3D data can be aggregated to a single value or be sliced/aggregated along any direction to obtain 2D view like previous technologies can, while also providing the ability of viewing the whole 3D information and switching between different views/locations without additional processing and can provide better accuracy than 2D. As used herein, an element or step recited in the singular and proceeded with the word "a" or "an" should be understood as not excluding plural elements or steps, unless such exclusion is explicitly recited. Furthermore, references to "one embodiment" of the present invention are not intended to be interpreted as excluding the existence of additional embodiments that also incorporate the recited features.

Control and processing methods and/or systems described herein may be implemented using computer programming or engineering techniques including computer software, firmware, hardware or any combination or subset thereof, wherein the technical effects may include at least processing of the three-dimensional data and diagnostic metrics according to the present disclosure.

Figure 12:
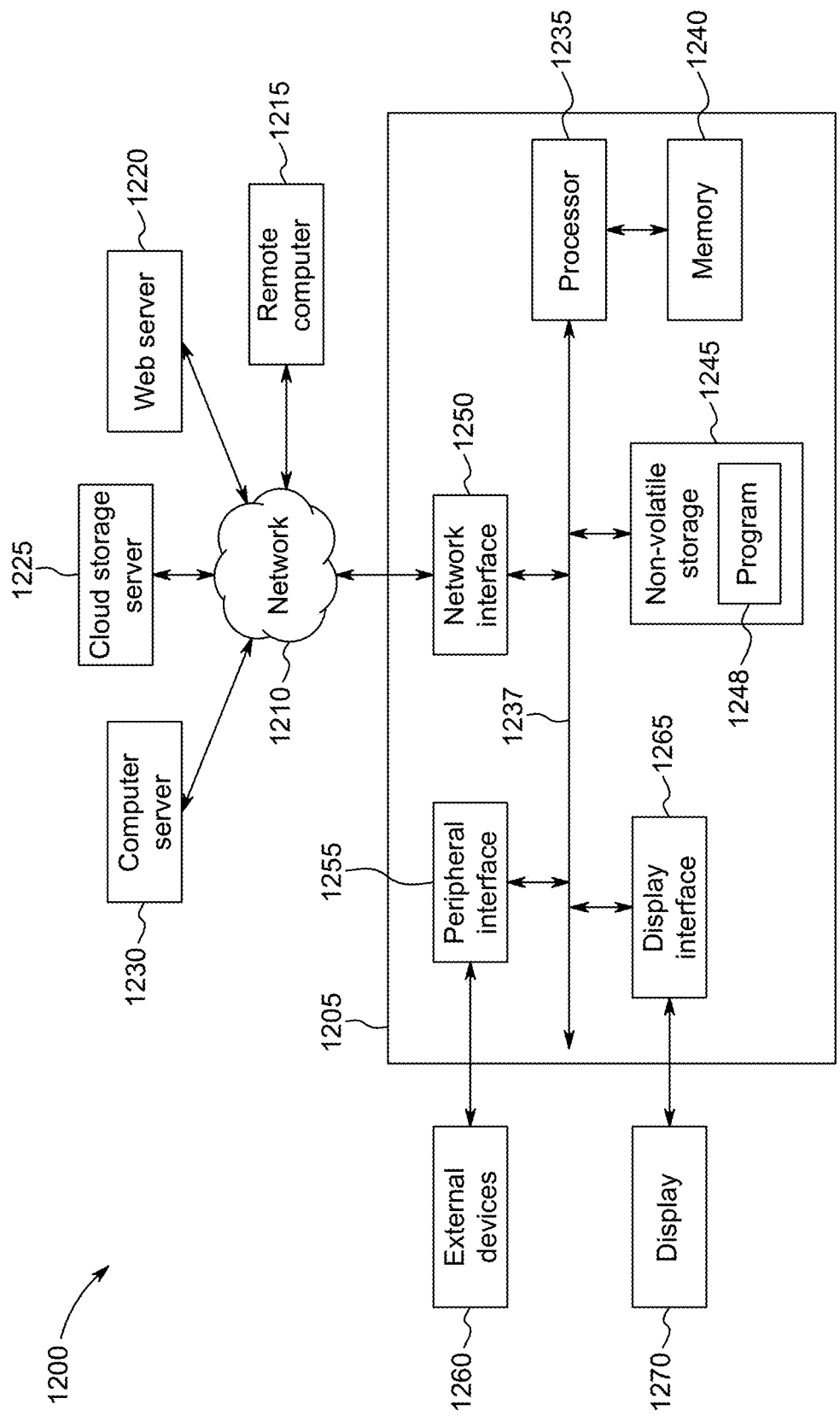
FIG. 12 shows a computer structure that may be used to implement an embodiment of the invention.

FIG. 12 illustrates a block diagram of a computer that may implement the various embodiments described herein. Control and processing aspects of the present disclosure may be embodied as a system, a method, and/or a computer program product. The computer program product may include a computer readable storage medium on which computer readable program instructions are recorded that may cause one or more processors to carry out aspects of the embodiment.

The computer readable storage medium may be a tangible and non-transitory device that can store instructions for use by an instruction execution device (processor). The computer readable storage medium may be, for example, but is not limited to, an electronic storage device, a magnetic storage device, an optical storage device, an electromagnetic storage device, a semiconductor storage device, or any appropriate combination of these devices. A non-exhaustive list of more specific examples of the computer readable storage medium includes each of the following (and appropriate combinations): flexible disk, hard disk, solid-state drive (SSD), random access memory (RAM), read-only memory (ROM), erasable programmable read-only memory (EPROM or Flash), static random access memory (SRAM), compact disc (CD or CD-ROM), digital versatile disk (DVD), MO, and memory card or stick. A computer readable storage medium, as used in this disclosure, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions implementing the functions described in this disclosure can be downloaded to an appropriate computing or processing device from a computer readable storage medium or to an external computer or external storage device via a global network (i.e., the Internet), a local area network, a wide area network and/or a wireless network. The network may include copper transmission wires, optical communication fibers, wireless transmission, routers, firewalls, switches, gateway computers and/or edge servers. A network adapter card or network interface in each computing or processing device may receive computer readable program instructions from the network and forward the computer readable program instructions for storage in a computer readable storage medium within the computing or processing device.

Computer readable program instructions for carrying out operations of the present disclosure may include machine language instructions and/or microcode, which may be compiled or interpreted from source code written in any combination of one or more programming languages, including assembly language, Basic, Fortran, Java, Python, R, C, C++, C# or similar programming languages. The computer readable program instructions may execute entirely on a user's personal computer, notebook computer, tablet, or smartphone, entirely on a remote computer or computer server, or any combination of these computing devices. The remote computer or computer server may be connected to the user's device or devices through a computer network, including a local area network or a wide area network, or a global network (i.e., the Internet). In some embodiments, electronic circuitry including, for example, programmable logic circuitry, field-programmable gate arrays (FPGA), or programmable logic arrays (PLA) may execute the computer readable program instructions by using information from the computer readable program instructions to configure or customize the electronic circuitry, in order to perform aspects of the present disclosure.

Aspects of the present disclosure are described herein with reference to flow diagrams and block diagrams of methods, apparatus (systems), and computer program products according to embodiments of the disclosure. It will be understood by those skilled in the art that each block of the flow diagrams and block diagrams, and combinations of blocks in the flow diagrams and block diagrams, can be implemented by computer readable program instructions.

The computer readable program instructions that may implement the systems and methods described in this disclosure may be provided to one or more processors (and/or one or more cores within a processor) of a general purpose computer, special purpose computer, or other programmable apparatus to produce a machine, such that the instructions, which execute via the processor of the computer or other programmable apparatus, create a system for implementing the functions specified in the flow diagrams and block diagrams in the present disclosure. These computer readable program instructions may also be stored in a computer readable storage medium that can direct a computer, a programmable apparatus, and/or other devices to function in a particular manner, such that the computer readable storage medium having stored instructions is an article of manufacture including instructions which implement aspects of the functions specified in the flow diagrams and block diagrams in the present disclosure.

The computer readable program instructions may also be loaded onto a computer, other programmable apparatus, or other device to cause a series of operational steps to be performed on the computer, other programmable apparatus or other device to produce a computer implemented process, such that the instructions which execute on the computer, other programmable apparatus, or other device implement the functions specified in the flow diagrams and block diagrams in the present disclosure.

FIG. 12 is a functional block diagram illustrating a networked system 1200 of one or more networked computers and servers. In an embodiment, the hardware and software environment illustrated in FIG. 12 may provide an exemplary platform for implementation of the software and/or methods according to the present disclosure. Referring to FIG. 12, a networked system 1200 may include, but is not limited to, computer 1205, network 1210, remote computer 1215, web server 1220, cloud storage server 1225 and computer server 1230. In some embodiments, multiple instances of one or more of the functional blocks illustrated in FIG. 12 may be employed.

Additional detail of a computer 1205 is also shown in FIG. 12. The functional blocks illustrated within computer 1205 are provided only to establish exemplary functionality and are not intended to be exhaustive. And while details are not provided for remote computer 1215, web server 1220, cloud storage server 1225 and computer server 1230, these other computers and devices may include similar functionality to that shown for computer 1205. Computer 1205 may be a personal computer (PC), a desktop computer, laptop computer, tablet computer, netbook computer, a personal digital assistant (PDA), a smart phone, or any other programmable electronic device capable of communicating with other devices on network 1210.

Computer 1205 may include processor 1235, bus 1237, memory 1240, non-volatile storage 1245, network interface 1250, peripheral interface 1255 and display interface 1265. Each of these functions may be implemented, in some embodiments, as individual electronic subsystems (integrated circuit chip or combination of chips and associated devices), or, in other embodiments, some combination of functions may be implemented on a single chip (sometimes called a system on chip or SoC).

Processor 1235 may be one or more single or multi-chip microprocessors, such as those designed and/or manufactured by Intel Corporation, Advanced Micro Devices, Inc. (AMD), Arm Holdings (Arm), Apple Computer, etc. Examples of microprocessors include Celeron, Pentium, Core i3, Core i5 and Core i7 from Intel Corporation; Opteron, Phenom, Athlon, Turion and Ryzen from AMD; and Cortex-A, Cortex-R and Cortex-M from Arm. Bus 1237 may be a proprietary or industry standard high-speed parallel or serial peripheral interconnect bus, such as ISA, PCI, PCI Express (PCI-e), AGP, and the like.

Memory 1240 and non-volatile storage 1245 may be computer-readable storage media. Memory 1240 may include any suitable volatile storage devices such as Dynamic Random Access Memory (DRAM) and Static Random Access Memory (SRAM). Non-volatile storage 1245 may include one or more of the following: flexible disk, hard disk, solid-state drive (SSD), read-only memory (ROM), erasable programmable read-only memory (EPROM or Flash), compact disc (CD or CD-ROM), digital versatile disk (DVD) and memory card or stick.

Program 1248 may be a collection of machine readable instructions and/or data that is stored in non-volatile storage 1245 and is used to create, manage and control certain software functions that are discussed in detail elsewhere in the present disclosure and illustrated in the drawings. In some embodiments, memory 1240 may be considerably faster than non-volatile storage 1245. In such embodiments, program 1248 may be transferred from non-volatile storage 1245 to memory 1240 prior to execution by processor 1235.

Computer 1205 may be capable of communicating and interacting with other computers via network 1210 through network interface 1250. Network 1210 may be, for example, a local area network (LAN), a wide area network (WAN) such as the Internet, or a combination of the two, and may include wired, wireless, or fiber optic connections. In general, network 1210 can be any combination of connections and protocols that support communications between two or more computers and related devices.

Peripheral interface 1255 may allow for input and output of data with other devices that may be connected locally with computer 1205. For example, peripheral interface 1255 may provide a connection to external devices 1260. External devices 1260 may include devices such as a keyboard, a mouse, a keypad, a touch screen, and/or other suitable input devices. External devices 1260 may also include portable computer-readable storage media such as, for example, thumb drives, portable optical or magnetic disks, and memory cards. Software and data used to practice embodiments of the present disclosure, for example, program 1248, may be stored on such portable computer-readable storage media. In such embodiments, software may be loaded onto non-volatile storage 1245 or, alternatively, directly into memory 1240 via peripheral interface 1255. Peripheral interface 1255 may use an industry standard connection, such as RS-232 or Universal Serial Bus (USB), to connect with external devices 1260.

Display interface 1265 may connect computer 1205 to display 1270. Display 1270 may be used, in some embodiments, to present a command line or graphical user interface to a user of computer 1205. Display interface 1265 may connect to display 1270 using one or more proprietary or industry standard connections, such as VGA, DVI, DisplayPort and HDMI.

As described above, network interface 1250, provides for communications with other computing and storage systems or devices external to computer 1205. Software programs and data discussed herein may be downloaded from, for example, remote computer 1215, web server 1220, cloud storage server 1225 and computer server 1230 to non-volatile storage 1245 through network interface 1250 and network 1210. Furthermore, the systems and methods described in this disclosure may be executed by one or more computers connected to computer 1205 through network interface 1250 and network 1210. For example, in some embodiments the systems and methods described in this disclosure may be executed by remote computer 1215, computer server 1230, or a combination of the interconnected computers on network 1210.

Data, datasets and/or databases employed in embodiments of the systems and methods described in this disclosure may be stored and or downloaded from remote computer 1215, web server 1220, cloud storage server 1225 and computer server 1230.

Numerous modifications and variations of the present invention are possible in light of the above teachings. It is therefore to be understood that within the scope of the appended claims, the invention may be practiced otherwise than as specifically described herein.

The invention claimed is:

1. A medical diagnostic apparatus, comprising:
 a receiver circuit that receives three-dimensional data of a subject's eye;
 a processor configured to separate portions of the three-dimensional data into separate segments, perform processing differently on each of the separate segments, and combine the separately processed segments to produce a segmented three-dimensional data set;
 the processor is further configured to generate at least one diagnostic metric from the segmented three-dimensional data set; and
 the processor is further configured to evaluate a medical condition based on the at least one diagnostic metric,
 wherein the processor is further configured to identify a reference plane maximally correlated with a largest surface of a Bruch's Membrane Opening in the subject's eye,
 the processor is further configured to identify a smooth polynomial maximally correlated with an anterior surface of a lamina cribrosa in the subject's eye, and the at least one diagnostic metric includes a measurement based on the reference plane and the smooth polynomial.

2. The medical diagnostic apparatus according to claim 1, wherein:
the processor is further configured to generate a visualization to render a three dimensional view of the diagnostic metric.

3. The medical diagnostic apparatus according to claim 1, wherein:
the at least one diagnostic metric includes at least one physical characteristic of a Bruch's Membrane Opening in the subject's eye.

4. The medical diagnostic apparatus according to claim 1, wherein:
the at least one diagnostic metric includes at least one physical characteristic of a lamina cribrosa in the subject's eye.

5. The medical diagnostic apparatus according to claim 1, wherein:
the at least one diagnostic metric includes at least one physical characteristic calculated based on a Bruch's Membrane Opening and a lamina cribrosa in the subject's eye.

6. The medical diagnostic apparatus according to claim 1, wherein:
the at least one diagnostic metric includes at least one of
a depth of a lowest point on an anterior surface of a lamina cribrosa in the subject's eye that is furthest from the reference plane,
a depth of a highest point on the anterior surface of the lamina cribrosa that is closest to the reference plane,
an X coordinate of the lowest point in an X/Y coordinate system of an optical coherence tomography scanner that generates the three-dimensional data,
a Y coordinate of the lowest point in the X/Y coordinate system,
an X coordinate of the highest point in the X/Y coordinate system,
a Y coordinate of the highest point in the X/Y coordinate system,
a volume of a space between the reference plane and the anterior surface of the lamina cribrosa,
an area of a contour of the Bruch's Membrane Opening projected to the reference plane,
an average depth of points on the anterior surface of the anterior surface of the lamina cribrosa with respect to the reference plane,
a mean of differences between each of the points on the anterior surface of the lamina cribrosa and corresponding points on a smooth curve approximation of the anterior surface of the lamina cribrosa,
a standard deviation of the differences,
a mean of line curvatures of lines that cross between the anterior surface of the lamina cribrosa and a vertical plane,
a standard deviation of the line curvatures,
a three-dimensional area of the anterior surface of the lamina cribrosa,
a two-dimensional area of a two-dimensional projection onto the reference plane of the anterior surface of the laminal cribrosa, and
a ratio of the three-dimensional area to the two-dimensional area.

7. The medical diagnostic apparatus according to claim 1, wherein:
the medical condition is glaucoma;

the at least one diagnostic metric includes at least one of
a depth of a lowest point on an anterior surface of a lamina cribrosa in the subject's eye that is furthest from the reference plane,
a depth of a highest point on the anterior surface of the lamina cribrosa that is closest to the reference plane,
an X coordinate of the lowest point in an X/Y coordinate system of an optical coherence tomography scanner that generates the three-dimensional data,
a Y coordinate of the lowest point in the X/Y coordinate system,
an X coordinate of the highest point in the X/Y coordinate system,
a Y coordinate of the highest point in the X/Y coordinate system,
a volume of a space between the reference plane and the anterior surface of the lamina cribrosa,
an area of a contour of the Bruch's Membrane Opening projected to the reference plane,
an average depth of points on the anterior surface of the anterior surface of the lamina cribrosa with respect to the reference plane,
a mean of differences between each of the points on the anterior surface of the lamina cribrosa and corresponding points on a smooth curve approximation of the anterior surface of the lamina cribrosa,
a standard deviation of the differences,
a mean of line curvatures of lines that cross between the anterior surface of the lamina cribrosa and a vertical plane,
a standard deviation of the line curvatures,
a three-dimensional area of the anterior surface of the lamina cribrosa,
a two-dimensional area of a two-dimensional projection onto the reference plane of the anterior surface of the laminal cribrosa, and
a ratio of the three-dimensional area to the two-dimensional area.

8. The medical diagnostic apparatus according to claim 1, wherein:
the medical condition is glaucoma;
the at least one diagnostic metric includes at least two of
a depth of a lowest point on an anterior surface of a lamina cribrosa in the subject's eye that is furthest from the reference plane,
a depth of a highest point on the anterior surface of the lamina cribrosa that is closest to the reference plane,
an X coordinate of the lowest point in an X/Y coordinate system of an optical coherence tomography scanner that generates the three-dimensional data,
a Y coordinate of the lowest point in the X/Y coordinate system,
an X coordinate of the highest point in the X/Y coordinate system,
a Y coordinate of the highest point in the X/Y coordinate system,
a volume of a space between the reference plane and the anterior surface of the lamina cribrosa,
an area of a contour of the Bruch's Membrane Opening projected to the reference plane,
an average depth of points on the anterior surface of the anterior surface of the lamina cribrosa with respect to the reference plane,
a mean of differences between each of the points on the anterior surface of the lamina cribrosa and corresponding points on a smooth curve approximation of the anterior surface of the lamina cribrosa, a standard deviation of the differences,
a mean of line curvatures of lines that cross between the anterior surface of the lamina cribrosa and a vertical plane,
a standard deviation of the line curvatures,
a three-dimensional area of the anterior surface of the lamina cribrosa,
a two-dimensional area of a two-dimensional projection onto the reference plane of the anterior surface of the laminal cribrosa, and
a ratio of the three-dimensional area to the two-dimensional area.

9. The medical diagnostic apparatus according to claim 1, wherein:
the medical condition is glaucoma;
the at least one diagnostic metric includes at least three of
a depth of a lowest point on an anterior surface of a lamina cribrosa in the subject's eye that is furthest from the reference plane,
a depth of a highest point on the anterior surface of the lamina cribrosa that is closest to the reference plane,
an X coordinate of the lowest point in an X/Y coordinate system of an optical coherence tomography scanner that generates the three-dimensional data,
a Y coordinate of the lowest point in the X/Y coordinate system,
an X coordinate of the highest point in the X/Y coordinate system,
a Y coordinate of the highest point in the X/Y coordinate system,
a volume of a space between the reference plane and the anterior surface of the lamina cribrosa,
an area of a contour of the Bruch's Membrane Opening projected to the reference plane,
an average depth of points on the anterior surface of the anterior surface of the lamina cribrosa with respect to the reference plane,
a mean of differences between each of the points on the anterior surface of the lamina cribrosa and corresponding points on a smooth curve approximation of the anterior surface of the lamina cribrosa,
a standard deviation of the differences,
a mean of line curvatures of lines that cross between the anterior surface of the lamina cribrosa and a vertical plane,
a standard deviation of the line curvatures,
a three-dimensional area of the anterior surface of the lamina cribrosa,
a two-dimensional area of a two-dimensional projection onto the reference plane of the anterior surface of the laminal cribrosa, and
a ratio of the three-dimensional area to the two-dimensional area.

10. The medical diagnostic apparatus according to claim 1, wherein:
the medical condition is glaucoma;
the at least one diagnostic metric includes at least four of
a depth of a lowest point on an anterior surface of a lamina cribrosa in the subject's eye that is furthest from the reference plane,
a depth of a highest point on the anterior surface of the lamina cribrosa that is closest to the reference plane,
an X coordinate of the lowest point in an X/Y coordinate system of an optical coherence tomography scanner that generates the three-dimensional data,
a Y coordinate of the lowest point in the X/Y coordinate system,
an X coordinate of the highest point in the X/Y coordinate system,
a Y coordinate of the highest point in the X/Y coordinate system,
a volume of a space between the reference plane and the anterior surface of the lamina cribrosa,
an area of a contour of the Bruch's Membrane Opening projected to the reference plane,
an average depth of points on the anterior surface of the anterior surface of the lamina cribrosa with respect to the reference plane,
a mean of differences between each of the points on the anterior surface of the lamina cribrosa and corresponding points on a smooth curve approximation of the anterior surface of the lamina cribrosa,
a standard deviation of the differences,
a mean of line curvatures of lines that cross between the anterior surface of the lamina cribrosa and a vertical plane,
a standard deviation of the line curvatures,
a three-dimensional area of the anterior surface of the lamina cribrosa,
a two-dimensional area of a two-dimensional projection onto the reference plane of the anterior surface of the laminal cribrosa, and
a ratio of the three-dimensional area to the two-dimensional area.

11. The medical diagnostic apparatus according to claim 1, wherein:
the medical condition is glaucoma;
the at least one diagnostic metric includes at least five of
a depth of a lowest point on an anterior surface of a lamina cribrosa in the subject's eye that is furthest from the reference plane,
a depth of a highest point on the anterior surface of the lamina cribrosa that is closest to the reference plane,
an X coordinate of the lowest point in an X/Y coordinate system of an optical coherence tomography scanner that generates the three-dimensional data,
a Y coordinate of the lowest point in the X/Y coordinate system,
an X coordinate of the highest point in the X/Y coordinate system,
a Y coordinate of the highest point in the X/Y coordinate system,
a volume of a space between the reference plane and the anterior surface of the lamina cribrosa,
an area of a contour of the Bruch's Membrane Opening projected to the reference plane,
an average depth of points on the anterior surface of the anterior surface of the lamina cribrosa with respect to the reference plane,
a mean of differences between each of the points on the anterior surface of the lamina cribrosa and corresponding points on a smooth curve approximation of the anterior surface of the lamina cribrosa,
a standard deviation of the differences,
a mean of line curvatures of lines that cross between the anterior surface of the lamina cribrosa and a vertical plane,
a standard deviation of the line curvatures,
a three-dimensional area of the anterior surface of the lamina cribrosa,
a two-dimensional area of a two-dimensional projection onto the reference plane of the anterior surface of the laminal cribrosa, and a ratio of the three-dimensional area to the two-dimensional area.

12. The medical diagnostic apparatus according to claim 1, wherein:
the medical condition is glaucoma;
the at least one diagnostic metric includes at least six of
a depth of a lowest point on an anterior surface of a lamina cribrosa in the subject's eye that is furthest from the reference plane,
a depth of a highest point on the anterior surface of the lamina cribrosa that is closest to the reference plane,
an X coordinate of the lowest point in an X/Y coordinate system of an optical coherence tomography scanner that generates the three-dimensional data,
a Y coordinate of the lowest point in the X/Y coordinate system,
an X coordinate of the highest point in the X/Y coordinate system,
a Y coordinate of the highest point in the X/Y coordinate system,
a volume of a space between the reference plane and the anterior surface of the lamina cribrosa,
an area of a contour of the Bruch's Membrane Opening projected to the reference plane,
an average depth of points on the anterior surface of the anterior surface of the lamina cribrosa with respect to the reference plane,
a mean of differences between each of the points on the anterior surface of the lamina cribrosa and corresponding points on a smooth curve approximation of the anterior surface of the lamina cribrosa,
a standard deviation of the differences,
a mean of line curvatures of lines that cross between the anterior surface of the lamina cribrosa and a vertical plane,
a standard deviation of the line curvatures,
a three-dimensional area of the anterior surface of the lamina cribrosa,
a two-dimensional area of a two-dimensional projection onto the reference plane of the anterior surface of the laminal cribrosa, and
a ratio of the three-dimensional area to the two-dimensional area.

13. The medical diagnostic apparatus according to claim 1, wherein:
the medical condition is glaucoma;
the at least one diagnostic metric includes each of
a depth of a lowest point on an anterior surface of a lamina cribrosa in the subject's eye that is furthest from the reference plane,
an X coordinate of the lowest point in an X/Y coordinate system of an optical coherence tomography scanner that generates the three-dimensional data,
a Y coordinate of the lowest point in the X/Y coordinate system,
a volume of a space between the reference plane and the anterior surface of the lamina cribrosa,
a mean of differences between each of the points on the anterior surface of the lamina cribrosa and corresponding points on a smooth curve approximation of the anterior surface of the lamina cribrosa,
a mean of line curvatures of lines that cross between the anterior surface of the lamina cribrosa and a vertical plane, and
a ratio of a three-dimensional area of the anterior surface of the lamina cribrosa to a two-dimensional area of a two-dimensional projection onto the reference plane of the anterior surface of the laminal cribrosa.

14. The medical diagnostic apparatus according to claim 1, wherein:
the medical condition is glaucoma;
the at least one diagnostic metric includes each of
a depth of a lowest point on an anterior surface of a lamina cribrosa in the subject's eye that is furthest from the reference plane,
a depth of a highest point on the anterior surface of the lamina cribrosa that is closest to the reference plane,
an X coordinate of the lowest point in an X/Y coordinate system of an optical coherence tomography scanner that generates the three-dimensional data,
a Y coordinate of the lowest point in the X/Y coordinate system,
an X coordinate of the highest point in the X/Y coordinate system,
a Y coordinate of the highest point in the X/Y coordinate system,
a volume of a space between the reference plane and the anterior surface of the lamina cribrosa,
an area of a contour of the Bruch's Membrane Opening projected to the reference plane,
an average depth of points on the anterior surface of the anterior surface of the lamina cribrosa with respect to the reference plane,
a mean of differences between each of the points on the anterior surface of the lamina cribrosa and corresponding points on a smooth curve approximation of the anterior surface of the lamina cribrosa,
a standard deviation of the differences,
a mean of line curvatures of lines that cross between the anterior surface of the lamina cribrosa and a vertical plane,
a standard deviation of the line curvatures,
a three-dimensional area of the anterior surface of the lamina cribrosa,
a two-dimensional area of a two-dimensional projection onto the reference plane of the anterior surface of the laminal cribrosa, and
a ratio of the three-dimensional area to the two-dimensional area.

15. The medical diagnostic apparatus according to claim 1, wherein:
the medical condition is an ocular or non-occular neuropathy;
the ocular neuropathy includes at least one of ischemic neuropathy, traumatic neuropathy, genetic neuropathy, inflammatory neuropathy, drug-induced neuropathy, congenital neuropathy, and pathologic myopia neuropathy;
the non-ocular neuropathy includes at least one of a brain tumor, intracerebral hemorrhage, brain trauma, brain abscess, meningitis, encephalitis, pseudotumor cerebri, a cerebrovascular disorder, and hypertension;
the processor is further configured to evaluate a progress or a risk of the ocular or non-occular neuropathy based on the at least one diagnostic metric including at least one of
a depth of a lowest point on an anterior surface of a lamina cribrosa in the subject's eye that is furthest from the reference plane,
a depth of a highest point on the anterior surface of the lamina cribrosa that is closest to the reference plane, an X coordinate of the lowest point in an X/Y coordinate system of an optical coherence tomography scanner that generates the three-dimensional data, a Y coordinate of the lowest point in the X/Y coordinate system, an X coordinate of the highest point in the X/Y coordinate system, a Y coordinate of the highest point in the X/Y coordinate system, a volume of a space between the reference plane and the anterior surface of the lamina cribrosa, an area of a contour of the Bruch's Membrane Opening projected to the reference plane, an average depth of points on the anterior surface of the anterior surface of the lamina cribrosa with respect to the reference plane, a mean of differences between each of the points on the anterior surface of the lamina cribrosa and corresponding points on a smooth curve approximation of the anterior surface of the lamina cribrosa, a standard deviation of the differences, a mean of line curvatures of lines that cross between the anterior surface of the lamina cribrosa and a vertical plane, a standard deviation of the line curvatures, a three-dimensional area of the anterior surface of the lamina cribrosa, a two-dimensional area of a two-dimensional projection onto the reference plane of the anterior surface of the laminal cribrosa, and a ratio of the three-dimensional area to the two-dimensional area.

16. The medical diagnostic apparatus according to claim 1, wherein:

the medical condition is an ocular or non-occular neuropathy;

the ocular neuropathy includes at least one of ischemic neuropathy, traumatic neuropathy, genetic neuropathy, inflammatory neuropathy, drug-induced neuropathy, congenital neuropathy, and pathologic myopia neuropathy;

the non-ocular neuropathy includes at least one of a brain tumor, intracerebral hemorrhage, brain trauma, brain abscess, meningitis, encephalitis, pseudotumor cerebri, a cerebrovascular disorder, and hypertension;

the processor is further configured to evaluate a progress or a risk of the ocular or non-occular neuropathy based on the at least one diagnostic metric including each of a depth of a lowest point on an anterior surface of a lamina cribrosa in the subject's eye that is furthest from the reference plane, an X coordinate of the lowest point in an X/Y coordinate system of an optical coherence tomography scanner that generates the three-dimensional data, a Y coordinate of the lowest point in the X/Y coordinate system, a volume of a space between the reference plane and the anterior surface of the lamina cribrosa, a mean of differences between each of the points on the anterior surface of the lamina cribrosa and corresponding points on a smooth curve approximation of the anterior surface of the lamina cribrosa, a mean of line curvatures of lines that cross between the anterior surface of the lamina cribrosa and a vertical plane, and a ratio of a three-dimensional area of the anterior surface of the lamina cribrosa to a two-dimensional area of a two-dimensional projection onto the reference plane of the anterior surface of the laminal cribrosa.

17. The medical diagnostic apparatus according to claim 1, wherein:

the medical condition is an ocular or non-occular neuropathy;

the ocular neuropathy includes at least one of ischemic neuropathy, traumatic neuropathy, genetic neuropathy, inflammatory neuropathy, drug-induced neuropathy, congenital neuropathy, and pathologic myopia neuropathy;

the non-ocular neuropathy includes at least one of a brain tumor, intracerebral hemorrhage, brain trauma, brain abscess, meningitis, encephalitis, pseudotumor cerebri, a cerebrovascular disorder, and hypertension;

the processor is further configured to evaluate a progress or a risk of the ocular or non-occular neuropathy based on the at least one diagnostic metric including each of a depth of a lowest point on an anterior surface of a lamina cribrosa in the subject's eye that is furthest from the reference plane, a depth of a highest point on the anterior surface of the lamina cribrosa that is closest to the reference plane, an X coordinate of the lowest point in an X/Y coordinate system of an optical coherence tomography scanner that generates the three-dimensional data, a Y coordinate of the lowest point in the X/Y coordinate system, an X coordinate of the highest point in the X/Y coordinate system, a Y coordinate of the highest point in the X/Y coordinate system, a volume of a space between the reference plane and the anterior surface of the lamina cribrosa, an area of a contour of the Bruch's Membrane Opening projected to the reference plane, an average depth of points on the anterior surface of the anterior surface of the lamina cribrosa with respect to the reference plane, a mean of differences between each of the points on the anterior surface of the lamina cribrosa and corresponding points on a smooth curve approximation of the anterior surface of the lamina cribrosa, a standard deviation of the differences, a mean of line curvatures of lines that cross between the anterior surface of the lamina cribrosa and a vertical plane, a standard deviation of the line curvatures, a three-dimensional area of the anterior surface of the lamina cribrosa, a two-dimensional area of a two-dimensional projection onto the reference plane of the anterior surface of the laminal cribrosa, and a ratio of the three-dimensional area to the two-dimensional area.

18. A method of medical diagnosis comprising:

obtaining three-dimensional data of a subject's eye;

separating portions of the three-dimensional data into separate segments;

performing processing differently on each of the separate segments;

combining the separately processed segments to produce a segmented three-dimensional data set;

generating at least one diagnostic metric from the segmented three-dimensional data set;

evaluating a medical condition based on the at least one diagnostic metric;

identifying a reference plane maximally correlated with a largest surface of a Bruch's Membrane Opening in the subject's eye; and identifying a smooth polynomial maximally correlated with an anterior surface of a lamina cribrosa in the subject's eye, wherein the at least one diagnostic metric includes a measurement based on the reference plane.

19. A non-transitory computer readable storage medium storing instructions, which when executed by a computer, performs steps comprising:

obtaining three-dimensional data of a subject's eye;

separating portions of the three-dimensional data into separate segments;

performing processing differently on each of the separate segments;

combining the separately processed segments to produce a segmented three-dimensional data set;

generating at least one diagnostic metric from the segmented three-dimensional data set;

evaluating a medical condition based on the at least one diagnostic metric; and identifying a reference plane maximally correlated with a largest surface of a Bruch's Membrane Opening in the subject's eye; and identifying a smooth polynomial maximally correlated with an anterior surface of a lamina cribrosa in the subject's eye, wherein the at least one diagnostic metric includes a measurement based on the reference plane.

\* \* \* \* \*